United States Patent
Leigh

(10) Patent No.: US 10,773,081 B2
(45) Date of Patent: Sep. 15, 2020

(54) IMPLANTABLE STIMULATING ASSEMBLY WITH LIMITED COMPONENTS

(71) Applicant: Charles Roger Aaron Leigh, Macquarie University (AU)

(72) Inventor: Charles Roger Aaron Leigh, Macquarie University (AU)

(73) Assignee: Cochlear Limited, Macquarie University, NSW (AU)

(*) Notice: Subject to any disclaimer, the term of this patent is extended or adjusted under 35 U.S.C. 154(b) by 9 days.

(21) Appl. No.: 15/248,120

(22) Filed: Aug. 26, 2016

(65) Prior Publication Data

US 2018/0056067 A1 Mar. 1, 2018

(51) Int. Cl.
*A61N 1/36* (2006.01)
*A61N 1/375* (2006.01)
*A61N 1/05* (2006.01)

(52) U.S. Cl.
CPC ..... *A61N 1/36036* (2017.08); *A61N 1/36017* (2013.01); *A61N 1/36038* (2017.08); *A61N 1/375* (2013.01); *A61N 1/0541* (2013.01); *A61N 1/3752* (2013.01)

(58) Field of Classification Search
CPC ............ A61N 1/36038; A61N 1/36032; A61N 1/36036; A61N 1/0541
See application file for complete search history.

(56) References Cited

U.S. PATENT DOCUMENTS

| 5,549,658 | A | * | 8/1996 | Shannon | A61N 1/36036 607/56 |
| 6,556,870 | B2 | | 4/2003 | Zierhofer et al. | |
| 2005/0033384 | A1 | * | 2/2005 | Sacha | A61N 1/36036 607/57 |
| 2006/0122664 | A1 | * | 6/2006 | Sacha | A61N 1/0541 607/57 |

* cited by examiner

*Primary Examiner* — Eric D. Bertram
(74) *Attorney, Agent, or Firm* — Pilloff Passino & Cosenza LLP; Martin J. Cosenza

(57) ABSTRACT

An electric hearing prosthesis, wherein the electric hearing prosthesis includes an implantable portion configured to electrically stimulate a cochlea to evoke a hearing percept, and an external portion configured to be in wired communication with the implantable portion, wherein the electronic components of the implantable portion are all passive electronic components.

22 Claims, 20 Drawing Sheets

IMPLANTABLE STIMULATING ASSEMBLY WITH LIMITED COMPONENTS

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

It is also noted that the electrode array of the cochlear implant generally shows utilitarian results if it is inserted in a cochlea.

SUMMARY

In accordance with an exemplary embodiment, there is a hearing prosthesis, comprising an electrode array of a cochlear implant configured to be implanted in a cochlea of a recipient, a lead assembly extending from the electrode array, and a connector located at an end of the lead assembly opposite the electrode array, wherein the lead assembly is a percutaneous lead assembly, and the connector is configured to place the lead assembly into wired communication with an external stimulator of the hearing prosthesis.

In accordance with an exemplary embodiment, there is a system, there is an electric hearing prosthesis, comprising an implantable portion configured to electrically stimulate a cochlea to evoke a hearing percept, and an external portion configured to be in wired communication with the implantable portion, wherein the electronic components of the implantable portion are all passive electronic components.

In accordance with another exemplary embodiment, there is a method, comprising accessing a middle ear cavity in a recipient, wherein the recipient includes a cochlea and a tympanic membrane, and implanting an assembly comprising an electrode array of a cochlear implant and an electrical lead assembly in wired communication with the electrode array in a recipient such that the lead assembly extends through the tympanic membrane and such that the electrode array, which includes a plurality of electrodes, is implanted in the cochlea such that a plurality of electrodes are located in the cochlea, wherein the plurality of electrodes are in wired communication with separate respective leads of the lead assembly.

BRIEF DESCRIPTION OF THE DRAWINGS

Embodiments of the present invention are described below with reference to the attached drawings, in which.

DETAILED DESCRIPTION

Figure 1A:
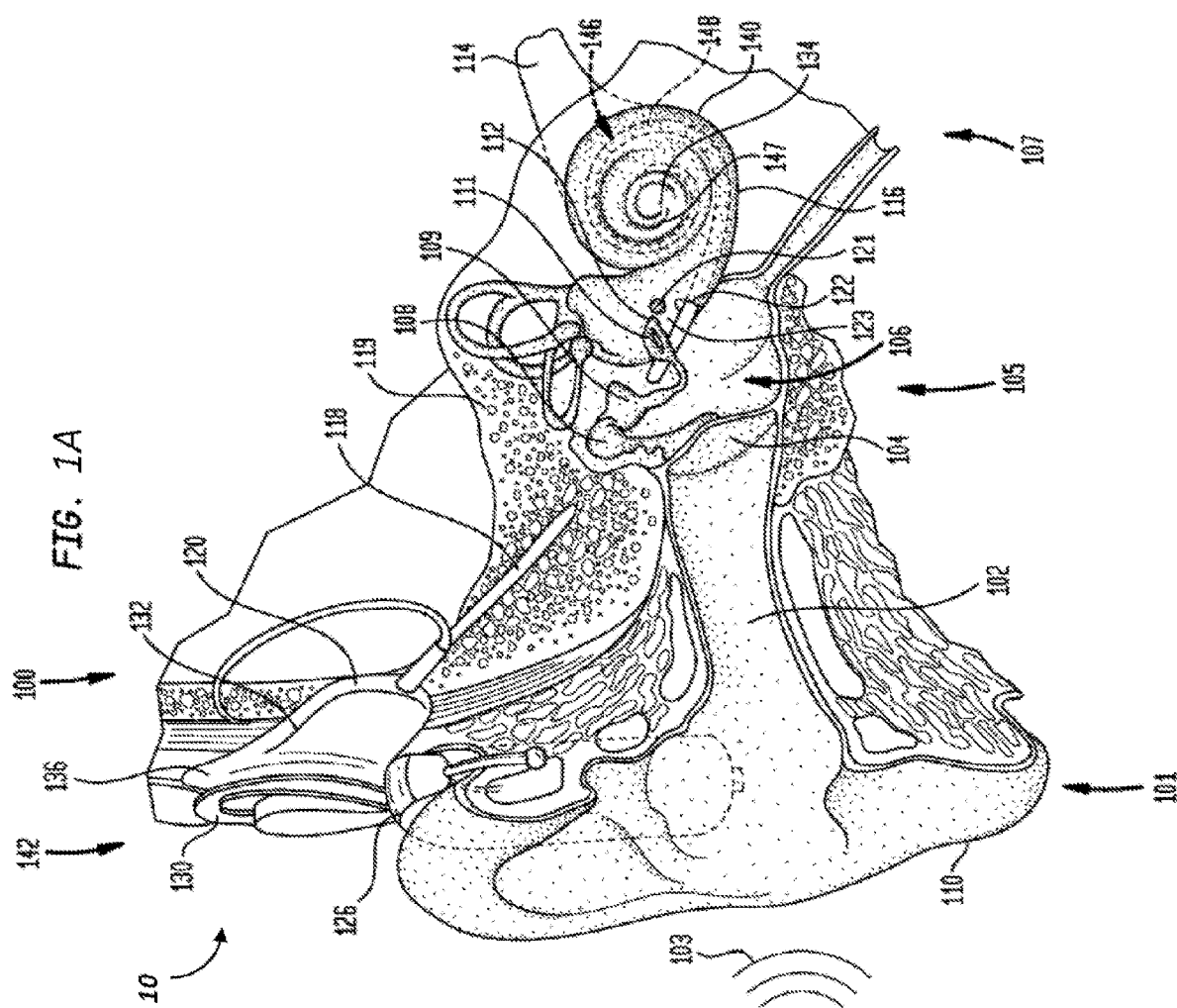
FIG. 1A is a perspective view of an exemplary hearing prosthesis utilized in some exemplary embodiments.

FIG. 1A is a perspective view of partially-implantable cochlear implant system 10 according to an exemplary embodiment, with a cochlear implant 100, implanted in a recipient. The cochlear implant 100 is part of a system 10 that includes an external component that includes a microphone and a sound processor. The sound processor processes signals from the microphone, and generates a signal that is transmitted transcutaneously to an implantable component which then uses the signal to stimulate tissue and evoke a hearing percept.

It is noted that in some conventional parlances, the entire system 10 is referred to as a cochlear implant, especially in the case of a cochlear implant that is not totally implantable. Herein, the phrase cochlear implant refers to the implantable component, and the phrase cochlear implant system refers to the entire system 10. That is, the phrase cochlear implant corresponds to the implantable component of a non-totally implantable cochlear implant system, which in the embodiment of FIG. 1A, includes a receiver-stimulator. It is further noted that the phrase "part of a cochlear implant" refers to a part of such an implant, where that part may or may not be, when used in its totality, a cochlear implant, unless otherwise specified (analogous to a swing comprising rope and a wheel of a truck—the wheel must be that of a truck, but it is not used as part of a truck).

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant.

In the illustrative arrangement of FIG. 1A, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand/or multi-strand platinum or gold wire or copper wire or tracks on a PCB. External device 142 also includes a magnet (not shown) positioned within the turns of wire of external coil 130. It should be appreciated that the external device shown in FIG. 1A is merely illustrative, and other external devices may be used with embodiments of the present invention.

In some embodiments, external device 142 includes a sound processing unit (not shown) to convert the sound signals received by the microphone of the BTE unit 126 into signals to be communicated via the inductive radio frequency communication link to the implanted component.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand/or multi-strand platinum or gold wire.

Cochlear implant 100 further comprises a main implantable component 120 and an elongate stimulating assembly 118. In embodiments of the present invention, internal energy transfer assembly 132 and main implantable component 120 are hermetically sealed within a biocompatible housing. Main implantable component 120 includes a stimulator unit (also not shown) which generates electrical stimulation signals based on the data signals. The electrical stimulation signals are delivered to the recipient via elongate stimulating assembly 118.

Elongate stimulating assembly 118 has a proximal end connected to main implantable component 120, and a distal end implanted in cochlea 140. Stimulating assembly 118 extends from main implantable component 120 to cochlea 140 through mastoid bone 119. In some embodiments, stimulating assembly 118 may be implanted at least in basal region 116, and sometimes further. For example, stimulating assembly 118 may extend towards apical end of cochlea 140, referred to as cochlea apex 134. In certain circumstances, stimulating assembly 118 may be inserted into cochlea 140 via a cochleostomy 122. In other circumstances, a cochleostomy may be formed through round window 121, oval window 112, the promontory 123, or through an apical turn 147 of cochlea 140.

Stimulating assembly 118 comprises a longitudinally aligned and distally extending array 146 of electrodes 148, disposed along a length thereof. As noted, a stimulator unit generates stimulation signals which are applied by stimulating contacts 148, which in an exemplary embodiment are electrodes, to cochlea 140, thereby stimulating auditory nerve 114. In an exemplary embodiment, stimulation contacts can be any type of component that stimulates the cochlea (e.g., mechanical components, such as piezoelectric devices that move or vibrate, thus stimulating the cochlea (e.g., by inducing movement of the fluid in the cochlea), electrodes that apply current to the cochlea, etc.). Embodiments detailed herein will generally be described in terms of a stimulating assembly 118 utilizing electrodes as elements 148. It is noted that alternate embodiments can utilize other types of stimulating devices. Any device, system, or method of stimulating the cochlea can be utilized in at least some embodiments.

Figure 1B:
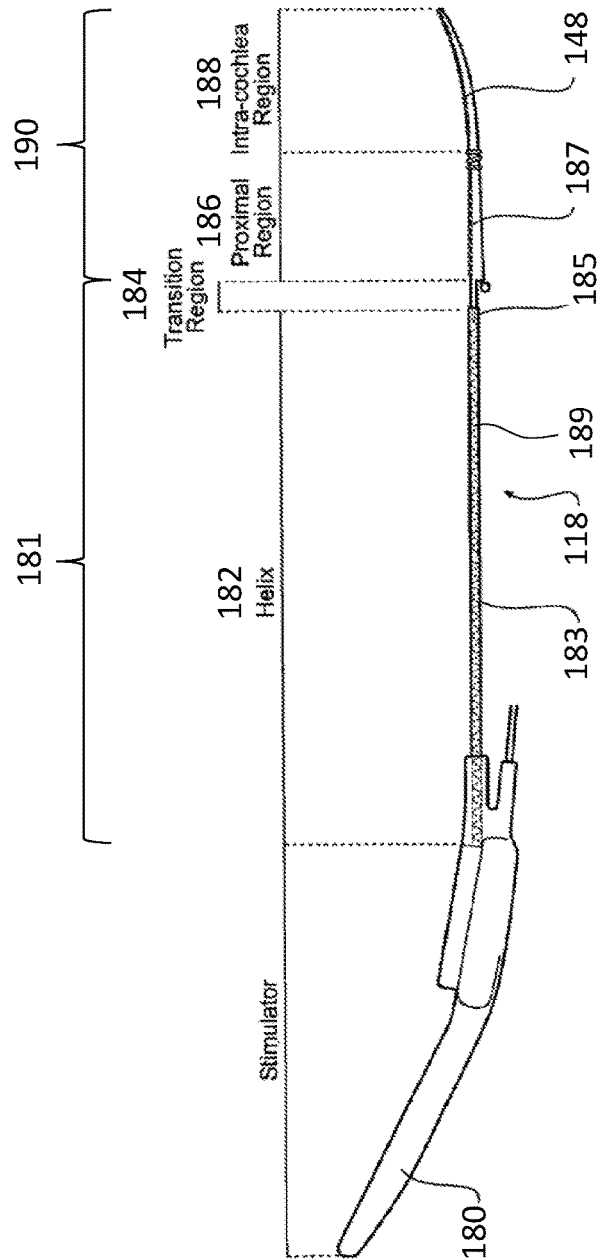
FIG. 1B is a side view of the implantable components of the cochlear implant illustrated in FIG. 1A.

Also, while embodiments disclosed herein are directed to electrodes, it is noted that in other embodiments, the teachings detailed herein are applicable to non-electrical stimulation, such as by way of example only and not by way of limitation, mechanical stimulation, optical stimulation, magnetic stimulation, middle ear acoustic implants (DACS) bone conduction devices, such as active bone conduction devices, etc. Indeed, in an exemplary embodiment, instead of, or in addition, to electrodes, induction coils are utilized to stimulate the tissue (e.g., the tissue inside the cochlea). Moreover, it is noted that embodiments disclosed herein are not limited to application to hearing prostheses. For example, the teachings detailed herein can be applicable to retinal stimulation, skin stimulation, etc. Further, it is noted that the teachings herein are applicable to stimulating medical devices having electrical stimulating electrodes of all types such as straight electrodes, perimodiolar electrodes and short/basal electrodes. Still focusing on a cochlear implant, FIG. 1B is a side view of the cochlear implant 100 without the other components of system 10 (e.g., the external components). Cochlear implant 100 comprises a receiver/stimulator 180 (combination of main implantable component 120 and internal energy transfer assembly 132) and an elongate stimulating assembly 118. Stimulating assembly 118 includes a helix region 182 that includes a body 183 in which is embedded (e.g., in the case where the body is silicone or another biocompatible material molded around wire leads) or otherwise containing (e.g., in the case where the body is a conduit or tube) electrical lead wires 189 in a helix (more on this below), a transition region 184 (which can be part of the body 183), a proximal region 186, and an intra-cochlear region 188. The proximal region 186, in this embodiment, is connected to the transition region 184 via a distinct connection 185, although in other embodiments, the transition region is blended into the helix region 182 (and the proximal region 186). Proximal region 186 and intra-cochlear region 188 form an electrode array 190. The portion of the stimulating assembly 118 that extends from the receiver/stimulator 180 to the electrode array 190 is referred to herein as the lead assembly, indicated by reference numeral 181 in FIG. 1B. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the stimulating assembly 118. In some exemplary embodiments, nubs 187 are provided on the outer surface of the proximal region to aid in the manipulation of the electrode array assembly 190 during insertion of the intra-cochlear region into the cochlea. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected to receiver/stimulator 180, through which respective stimulating electrical signals for each electrode contact 148 travel.

It is noted that in some embodiments, the helix region 182 does not extend as far as that depicted in FIG. 1B, and the transition region 184 is thus longer. That is, in some exemplary embodiments, the helix region 182 does not extend substantially the full length between the receiver/stimulator 180 and the proximal region 186, but instead extends less than that (e.g., about half the distance), where the remaining distance is established by substantially straight lead wires, or at least wires that are not substantially helixed. Any arrangement of lead wires that can enable the teachings detailed herein and/or variations thereof to be practiced can be utilized in some exemplary embodiments.

Figure 2:
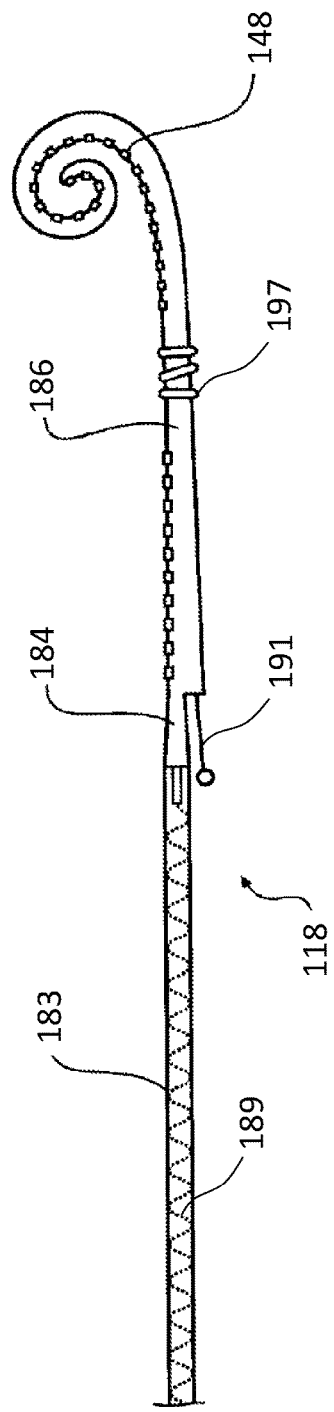
FIG. 2 is a side view of an embodiment of the electrode array illustrated in FIGS. 1A and 1B in a curled orientation.

FIG. 2 is a side view of a portion of stimulating assembly 118 where the electrode array of the electrode array assembly 190 is in a curled orientation, as it would be when inserted in a recipient's cochlea, with electrode contacts 148 located on the inside of the curve.

It is noted that FIGS. 1B and 2 can be, by way of example only and not by way of limitation, a lateral wall, a perimodiolar stimulating assembly or a mid-scala assembly which assumes a mid-scala position during or following implantation.

It is noted that the embodiment of FIG. 2 is depicted with a removable stylus 191 that maintains a pre-curved intra-cochlea region of the electrode array assembly in a more straightened configuration, such that upon removal of the stylus 191, the intra-cochlea region 188 curls. Embodiments can be practiced with and without the stylus configuration. Embodiments can be practiced with pre-curled arrays and straight arrays.

Figure 3A:
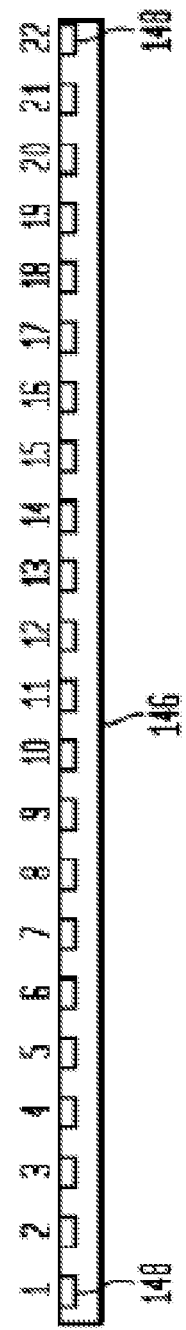
FIG. 3A is a functional schematic of an electrode array including 22 electrodes spaced apart from one another.

FIG. 3A illustrates a more detailed view, albeit functionally, of an exemplary electrode array 146 comprising a plurality of electrodes 148 labeled 1-22, in accordance with an embodiment. In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel). Briefly, it is noted that during stimulation by the electrodes to evoke a hearing percept, one or more electrodes 148 is activated at a given electrode stimulation level (e.g., current level).

The receiver/stimulator 180 of FIG. 1B is an implantable portion of the electric hearing prosthesis of FIG. 1B. The receiver/stimulator 180 is present in the implantable portion because of the transcutaneous communication between the implantable component of the hearing prosthesis and the external component wirelessly through the skin of the recipient. In this regard, the external RF coil of the external component provides signal and/or power to the implantable component via the implantable coil of the receiver/stimulator unit 180. The stimulator portion of the receiver/stimulator unit 180 receives the signal from the coil thereof and converts the signal into stimulation signals that are provided via the leads 189 to the electrodes so as to electrically stimulate the cochlea to evoke a hearing percept.

Figure 3B:
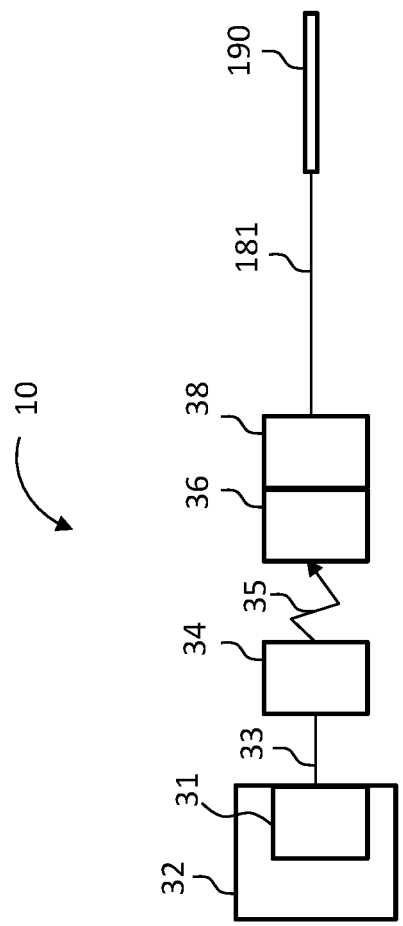
FIG. 3B is a functional block diagram schematic of the system 10 of FIG. 1A.

Functionally, the components of FIG. 1B are represented in FIG. 3B, along with the external components of the hearing prosthesis system 10. More particularly, element 32 of FIG. 3B represents the BTE device 126 of the external portion of the hearing prosthesis of system 10, where element 31 represents the sound processor thereof, which processes captured sound captured by the microphone and ferns that sound into electronic signal that are communicated via element 33, which represents the lead assembly extending from the BTE device 126, to the external RF inductance coil, which coil is represented by element 34. As shown, link 35 represents the transcutaneous inductance link between the external coil in the implanted coil of the implanted receiver, represented by element 36. Element 38 represents the implanted stimulator, which stimulator receive signals from the implanted receiver 36 and converts those signals into stimulation signals that are supplied via the lead assembly 181 to the electrode array assembly 190 in general, and the electrode contacts thereof in particular, so as to stimulate the cochlea and evoke a hearing percept thereby. Collectively, elements 36 and 38 represent the receiver/stimulator 180 of the implantable component of FIG. 1B.

In an alternate embodiment, the receiver portions of the receiver/stimulator unit 180 are done away with, and the stimulator portion thereof is located in an external component (if present at all—in other embodiments, stimulation is directly applied from a sound processor or the like—more on this below). That is, in an exemplary embodiment, the implantable portion of the hearing prosthesis can include, in its entirety, the portions downrange from the receiver/stimulator unit 180/the portions to the right of the lead assembly 181 and inclusive of at least a portion of the lead assembly 181, and/or some additional ancillary portions (e.g., components to hold the electrode array assembly 190 in place, a connector potentially, etc.). In an exemplary embodiment, all other portions of the hearing prosthesis are located external to the recipient.

Figure 4:
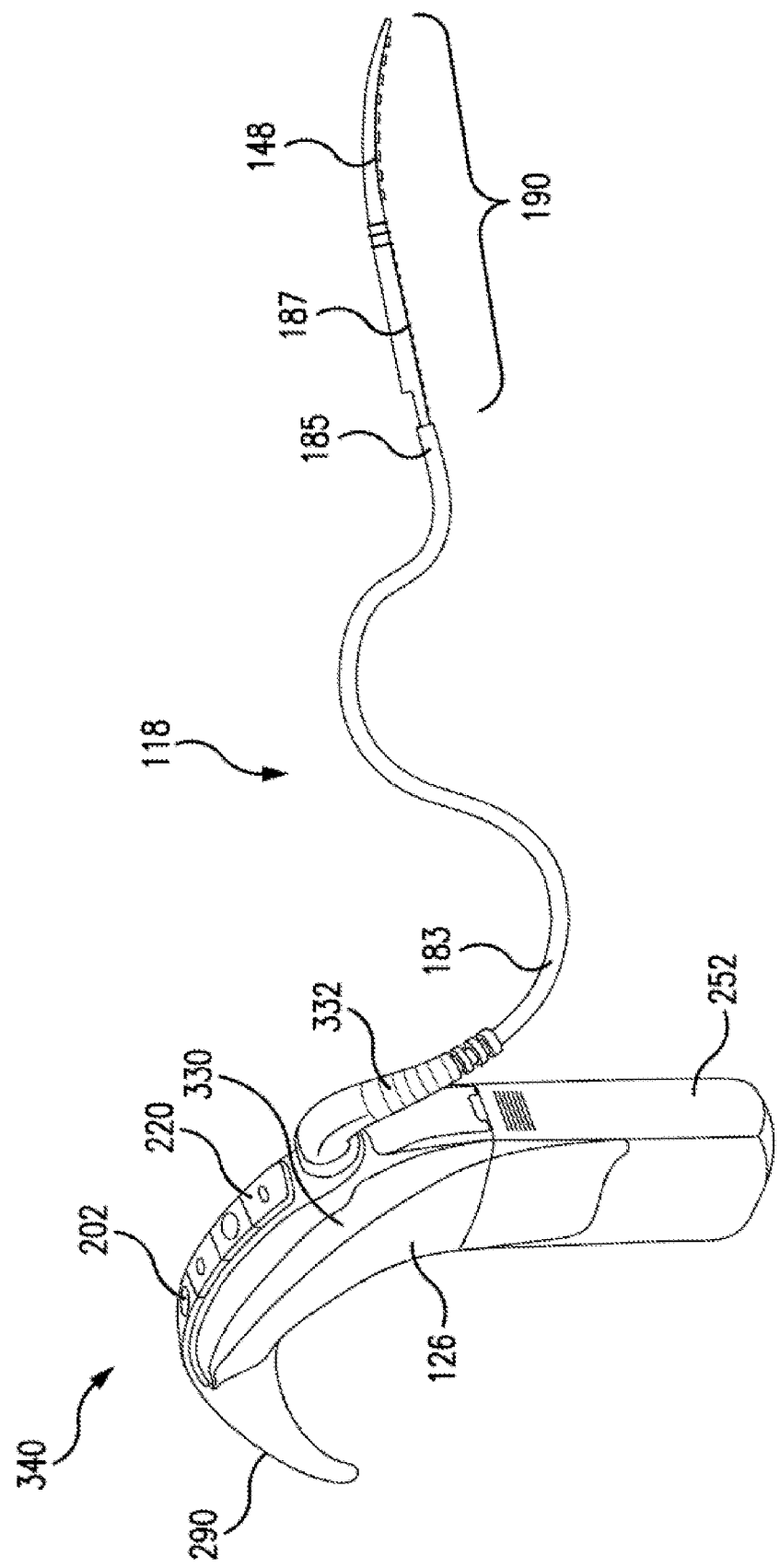
FIG. 4 is a perspective view of an exemplary electric hearing system.

In this vein, FIG. 4 depicts an exemplary embodiment of an electrical hearing prosthesis embodiment that includes an external device 340 that is part of an external portion of the hearing prosthesis, which can correspond to, at least in part, for example, the device of FIG. 1A, but with additional functionality and/or less functionality and/or additional features and/or less features as will be described below. The electric hearing prosthesis further includes an implantable portion in wired communication with the external device 340, which implantable component includes the electrode array assembly 190, and a portion of the body 183 (depending on how much is implanted, more on this below), which can variously correspond to the elongate stimulating assembly 118.

Electrode array assembly 190 is in wired electronic communication with spine 330 of the BTE device 340 via elongate stimulating assembly 118 in general, and the lead wires 189 in particular. In at least some exemplary embodiments, the spine 330 of the BTE contains a sound processor/sound processing unit or the like.

Also, in an exemplary embodiment, the spine 330 of the BTE contains a stimulator unit that converts the output of the sound processor into signals that are provided via the lead wires 189 to the electrode contacts of the electrode array assembly 190. Thus, the stimulator portion of the cochlear implant of FIG. 1B is located inside otherwise is part of the external component as opposed to being implanted in the recipient. It is noted that in an exemplary embodiment, the stimulator unit can be a separate component from the sound processor, while in an alternate embodiment, the stimulator unit can be an integral apparatus with the sound processor.

Figure 5:
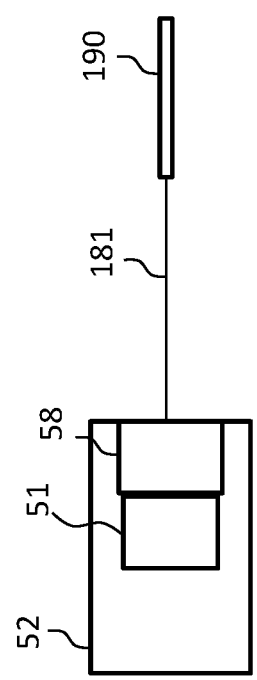
FIGS. 5-8 are functional block diagrams detailing features of various embodiments.

In this regard, relying on the functional components of FIG. 3B above, FIG. 5 depicts an exemplary functional diagram of the embodiment of FIG. 4, wherein element 52 represents the BTE device 126, element 51 again represents the sound processor, element 58 represents the stimulator, element 181 represents the lead assembly, an element 190 represents the electrode array assembly. Thus, the embodiment of FIG. 4 can utilize components of the system 10 in a modified manner so as to operate according to the teachings detailed herein. It is further noted that in at least some exemplary embodiments, there is no separate stimulator 58. Instead, the output of the sound processor 51 is sufficient to provide a stimulation signal to the electrode contacts of the electrode array assembly 190.

BTE device 340 includes one or more microphones 202, and may further include an audio signal jack 210 under a cover 220 on the spine 330 of BTE device 340. It is noted that in some other embodiments, one or both of these components (microphone 202 and/or jack 210) may be located on other positions of the BTE device 340, such as, for example, the side of the spine 330, the ear hook 290, etc. FIG. 4 further depicts battery 252 and ear hook 290 removably attached to spine 330.

It is noted that while the embodiment of FIG. 4 depicts the microphone being located on the spine 330 at about the apex thereof, in an alternate embodiment, the microphone can be located elsewhere. It is further noted that the microphone can be located on the ear hook 290 anywhere from and including the tip thereof to the location where the ear hook interfaces with the spine. Such is also the case with respect to the microphone located on the spine 330—the microphone can be located anywhere on the spine from the interface of the spine in the ear hook 290 to the interface of the battery 252 with the spine 330. Still further, BTE device 575 can include a plurality of microphones located according to the various teachings detailed herein and/or variations thereof. Any microphone placement that can enable the teachings detailed herein and/or variations thereof to be practiced can be utilized in at least some exemplary embodiments.

FIG. 4 depicts a break in the electrical leads extending from spine 330 to the electrode array assembly 190. This is depicted for schematic reasons only so as to conserve space, as in at least the embodiment of FIG. 4, the leads extend uninterrupted from the spine 330 (or more accurately, from the connector 332 connected to the spine 330) to the electrode array assembly 190. Additional details of this will be described below, although it is briefly noted that in an exemplary embodiment, the portion that is depicted as the break in FIG. 4 can correspond to about the location where the lead assembly 181 extends from inside the recipient to the outside of the recipient.

Figure 6:
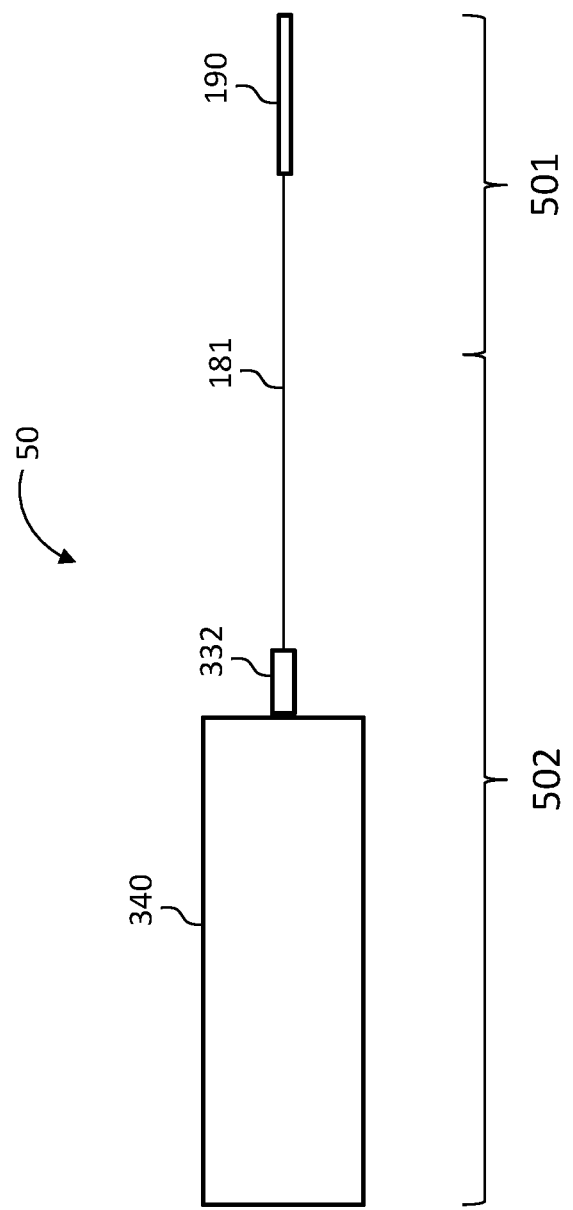

FIG. 6 depicts a functional diagram of a system 50 which corresponds to the electric hearing prosthesis of FIG. 4 above. For the purposes of the following discussions, reference will be made to functional diagrams for purposes of linguistic simplicity and economy of language.

More particularly, system 50 includes the electrode array assembly 190, the lead assembly 181, connector 332, and the external device 340, which corresponds to the BTE device noted above, where connector 332 places the lead assembly 181 into signal communication with the external device 340 in general, and the spine 330 of the external device 340 in particular.

Figure 7:
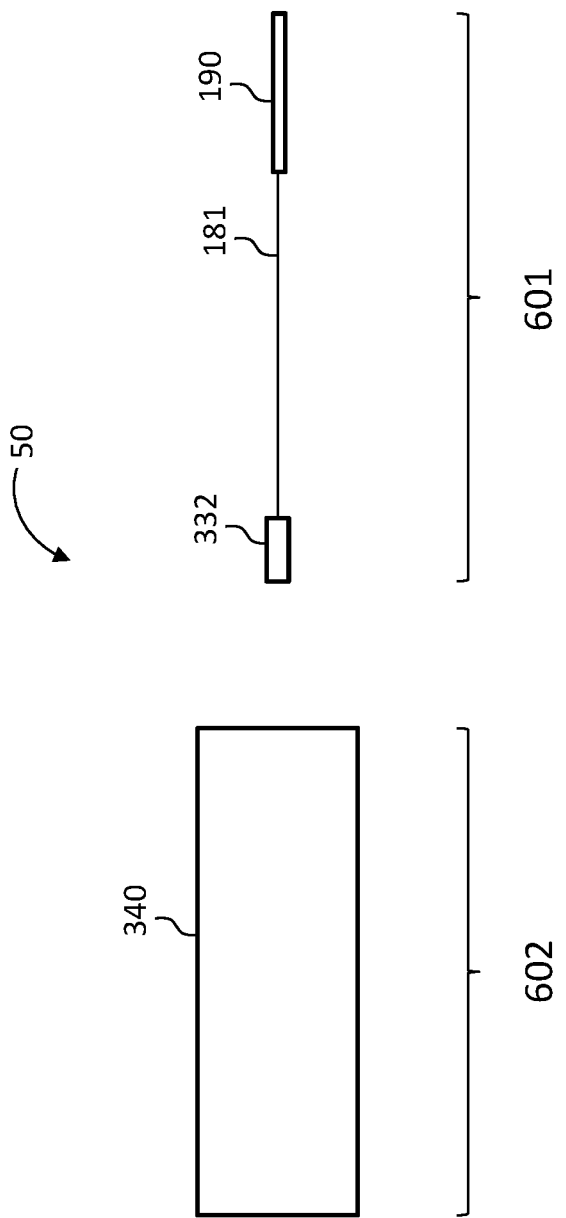

System 50 has been identified in terms of two different sections: an implantable portion 501 and an external portion 502. In the embodiment of FIG. 6, there is no exact demarcation between the implantable portion 501 and the external portion 502, while in other embodiments, such as those that include a stop with the like on the lead assembly 801 (which stop abuts the tympanic membrane as will be described in greater detail below), the implantable portion 501 and the external portion 502 has more than exact demarcation between those portions. This is as opposed to considering the system 50 in terms of an implantable component 601 and an external component 602, such as seen in FIG. 7, which shows those component detached from one another (connector 332 has been disconnected from the external device 340). In this regard, the implantable component 601, in use, has a portion that is external to the recipient. Thus, an implantable component as that term is used herein does not exclude a portion that is not implanted in use in the recipient. In this regard, the phrase implantable component is a component of the hearing prostheses where at least a portion thereof is configured to be implanted into a recipient (e.g., the implantable portion 501), and has structure that is biocompatible with such. This is as opposed to the connector 332, which may not necessarily be biocompatible or otherwise configured to be implanted into the recipient, even though it is part of the implantable component 601.

In working use, beyond that which results from destructively severing one component from the other, the system 50 can be separated in use as shown in FIG. 7. In particular, the connector 332 is configured to relatively easily connect and disconnect to/from the external device 340.

Figure 8:
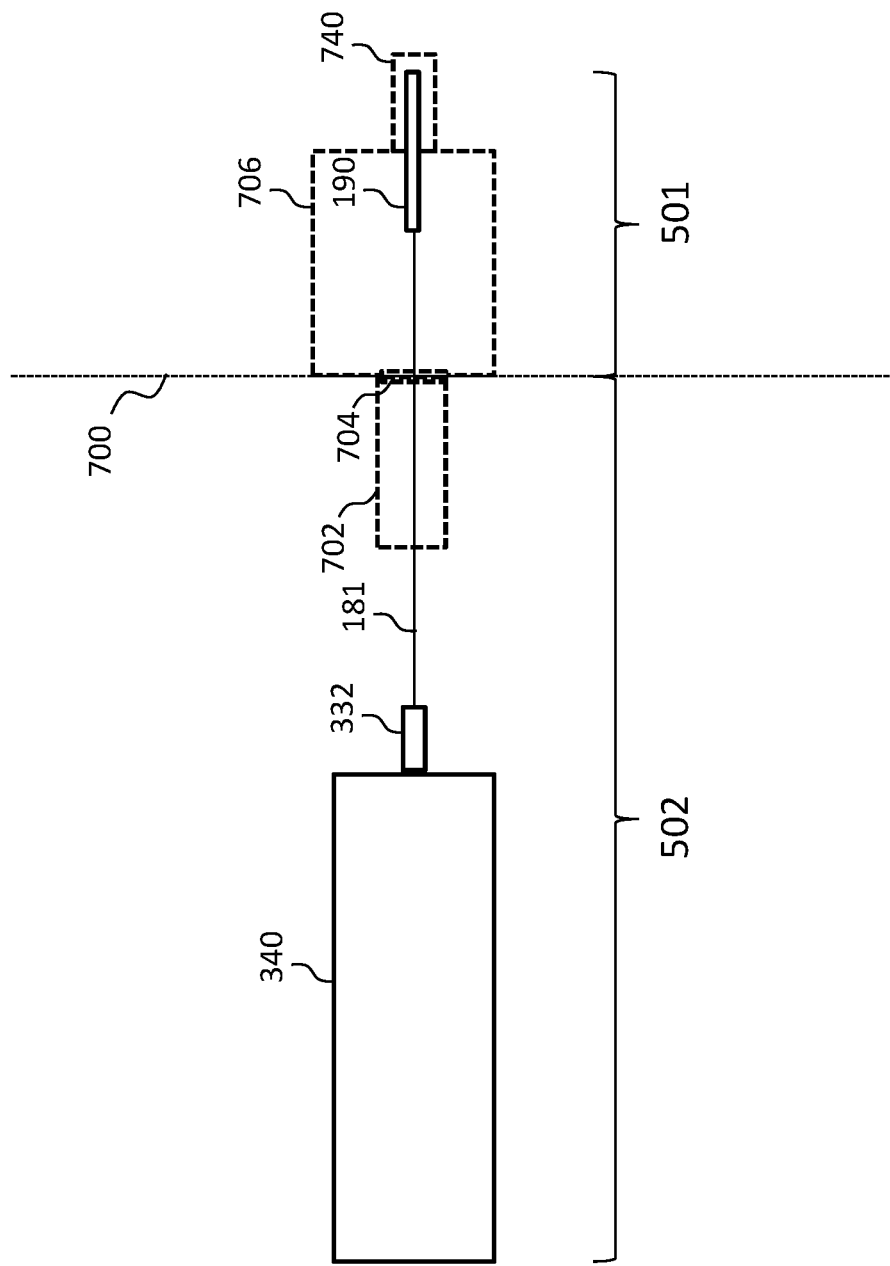

An exemplary embodiment of the system 50 is such that, when the electrode array assembly 190 is implanted into the cochlea, lead assembly 181 extends through the tympanic membrane to the outside of the recipient, and thus to connector 332, which is connected to the BTE device 340. In this regard, all of the active electrical components are located outside of the recipient/are located in external portions of the electric hearing prostheses (the system 50). FIG. 8 functionally depicts portions of a human body superimposed upon the system 50, thus representing a function of version of system 50 and use, or portion thereof is implanted into the recipient. More specifically, block diagram 740 represents the cochlea of the recipient, which corresponds to element 140 of FIG. 1A above. Block diagram 706 represents the middle ear, and corresponds to elements 106 of FIG. 1A above. Block diagram 704 represents the tympanic membrane and corresponds to element 104 of FIG. 1A above. Block diagram 702 represents the ear canal/outer ear, and thus corresponds to element 102 of FIG. 1A above. Line 700 represents the skin of the recipient. In the embodiment of FIG. 8, components to the right of line 700, more accurately, portions of the system 50 to the right of line 700, are implanted in the recipient, and portions to the left of line 700 are not implanted into the recipient.

Thus, in view of the above, there is a hearing prosthesis, comprising an electrode array of a cochlear implant, such as electrode array assembly 190, configured to be implanted in a cochlea of a recipient. The prosthesis further includes a lead assembly, such as lead assembly 181, extending from the electrode array, and a connector, such as connector 332, located at an end of the lead assembly opposite the electrode array. The lead assembly is a percutaneous lead assembly in that the lead assembly is configured to extend from outside the skin of the recipient to under the skin of the recipient inside the recipient. Further, the connector is configured to place the lead assembly into wired communication with an external stimulator of the hearing prosthesis, such as external component 340 (whether such uses a dedicated stimulator 58 or a sound processor 51 where the signals from the sound processor 51 are used to stimulate the electrodes, etc.).

As will be understood from the above, in an exemplary embodiment, the hearing prosthesis includes a BTE device, wherein the connector is connected to the BTE device as will be described in greater detail below, in an alternate embodiment, the prosthesis includes an ITE device (In-The-Ear device), and the connector is connected to the ITE device. In some ITE device embodiments, all of the functionalities of the BTE device are present in the ITE device, while in some other ITE device embodiments, only some of the functionalities of the BTE device are present in the ITE device. In at least some exemplary embodiments, the ITE device includes a sound processor and a stimulator (if the stimulator is a separate component from the sound processor) and, in some embodiments, a microphone.

Also as will be understood from the above, in an exemplary embodiment, the hearing prosthesis further includes an external sound processor, such as sound processor 51, wherein the hearing prosthesis does not include an RF communication component placing the sound processor into signal communication with the electrodes of the electrode array. This is because with respect to the embodiments detailed above, the transcutaneous inductance link is done away with, and the electrode array assembly 190 is in wired communication with the external component in general, and the sound processor thereof in particular. Note that by "wired communication with the sound processor," this can include an embodiment where there is no stimulator component interposed between the sound processor and the electrode array assembly, and an embodiment where there is a stimulator component interposed between the sound processor and the electrode array assembly, the latter being a scenario where the electrode array assembly is indirectly in wired signal communication with the sound processor.

Figure 9:
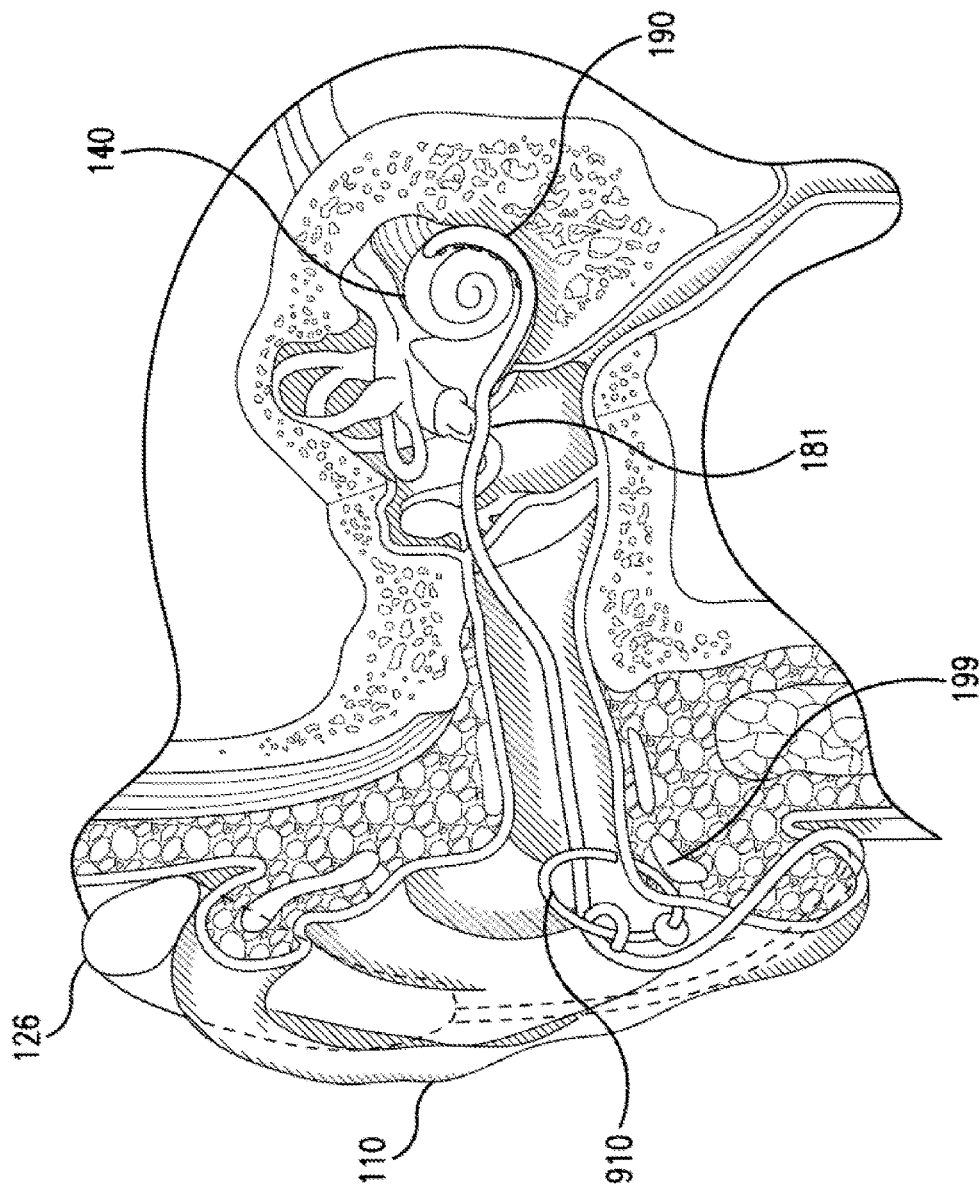
FIGS. 9-13 are schematics of various lead assembly retention components.
Figure 10:
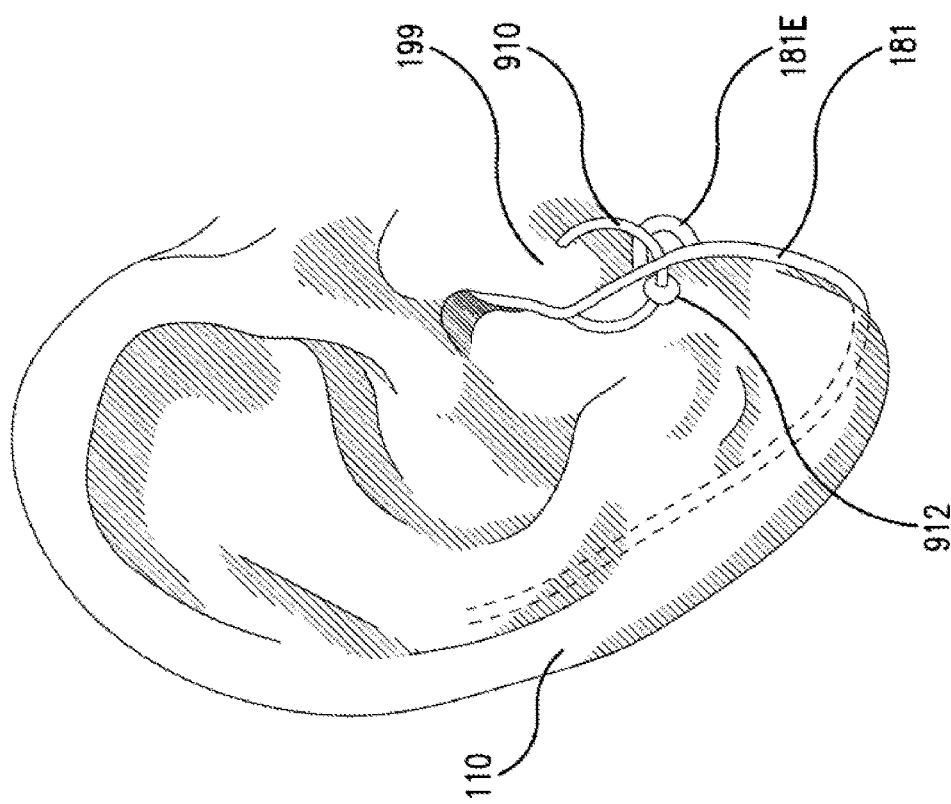

There can be utilitarian value with respect to fixing the lead assembly to the skin of the recipient. Such utilitarian value can relate to preventing or otherwise limiting movement of the lead assembly 181, and thus the electrode array assembly 190 relative to the tissue of the recipient. In this regard, in at least some exemplary embodiments, fixing the lead assembly to the skin of the recipient can limit or otherwise prevent movement of the electrode array assembly 190 within the cochlea due to, for example, forces acting on the lead assembly 181, which forces can be generated at locations and applied to the lead assembly 181 at locations outside of the recipient relative to the tympanic membrane 104, such as in a scenario where the BTE device 126 is taken off the pinna 110 while still connected to the lead assembly 181 and attempted to be moved a distance from the pinna 110 beyond that which would be "permitted" by the lead assembly 181. FIG. 9 depicts an exemplary embodiment of the system 50 utilizing a fixation component 910. As can be seen, fixation component/fixation device (sometimes herein referred to as a connector) 910 is a ring extending through the tragus of the outer ear. The lead assembly 181 extends through the ring. In the embodiment depicted in FIG. 9, the portion of the lead assembly 181 proximate the ring 910 is fixed to the ring 910 such that the lead assembly 181 cannot move in the longitudinal direction and with the lateral directions beyond that which is permitted by the ring 910. In an exemplary embodiment, the lead assembly 181 is glued to the ring 910. In an exemplary embodiment, lead assembly 181 is molded around the ring 910. In this regard, the body 183 of the lead assembly can be thicker in the areas proximate to the ring 910, thus permitting the ring to extend through a hole in the second area. This concept is seen in FIG. 10, where "extra area" 181E has been added to the sheathing of the lead assembly such that a hole can be present in the extra area 181E through which the ring 910 extends, thus limiting the movement of the lead assembly 181 to the movements of the ring 910 relative to the tragus 199. As can be seen, the ring 910 includes a stop at 912 located on the far side of the ring relative to the viewer's perspective of FIG. 10. In an exemplary embodiment, a stop can be located on the near side of the ring 912 as well. Note also that instead of acting as a stop, element 912 can act as the traditional ring closure component of the ring 910.

While the embodiment depicted in FIG. 10 provides a ring that has a relatively large amount of clearance relative to the tragus 199, in an alternate embodiment, the general diameter of the ring 910 can be smaller than that depicted in FIG. 10, thus limiting the amount of clearance relative to the tragus 199. Indeed, as noted above, in an exemplary embodiment, the leads of the lead assembly 181 can pass through the ring 910, and the ring 910 can create a quasi-compression fit between the outside of the lead assembly 181 and the skin of the recipient, thus utilizing friction forces to secure the lead assembly 181 in place. That said, in an alternate embodiment, this arrangement can be combined with the embodiment depicted in FIG. 10 and/or in another arrangement (e.g., where the ring 910 is glued or otherwise adhered to the lead assembly 181). Any arrangement that will connect the lead assembly 181 to the ring 910 that will limit the movement of the lead assembly 181 so as to have utilitarian value of limiting the likelihood that the electrode array assembly 190 will be pulled out of the cochlea can be utilized in at least some exemplary embodiments.

Figure 12:
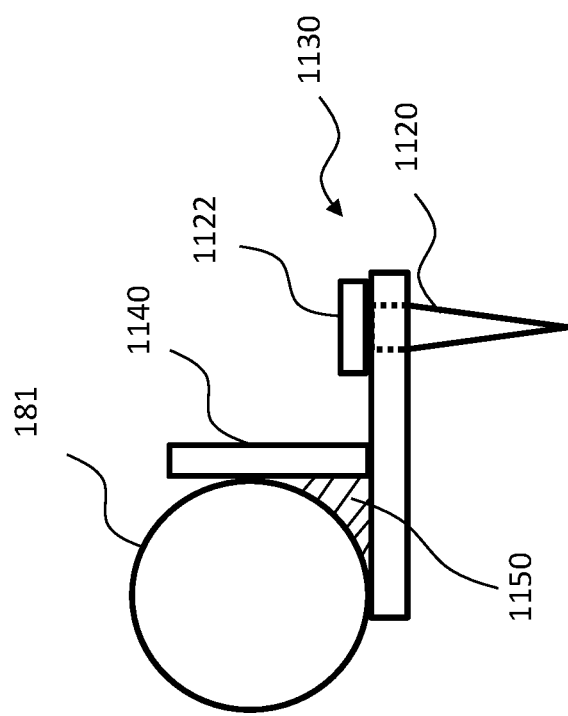

While the embodiment depicted in FIGS. 9 and 10 are centered around a percutaneous ring, in other embodiments, a clip is utilized that clips onto the tragus instead of piercing the tragus. Also, instead of a ring, a stud or the like can be utilized. An example of this is depicted in FIG. 12. As shown in FIG. 12, there is a stud 1030 that includes a shaft 1020 configured to penetrate the tragus. A screw type or clip type stop 1022 is provided at one end of the shaft 1020, and a clip 1030 is located at the other end of the shaft 1020. In use, the stop 1022 is removed from the shaft 1020, and the shaft 1020 is inserted through a piercing of the tragus from the ear canal side, such that the clip 1030 is located on the far side of the tragus with respect to the view of FIG. 10. To secure the stud 1030 in place, the stop 1022 is reattached to the shaft 1020, such that the stop 1022 lies on the outside surface of the tragus, and is between the tragus and the viewer with respect to the frame of reference of FIG. 10. Subsequently to this, the lead assembly 181 is inserted into the inside of the clip 1030, as shown in FIG. 12. Owing to a resiliency of the clip 1030, the clip and grips the lead assembly 181, and thus holds the lead assembly 181 relative to the stud 1030. In other embodiments, adhesive or the like can be utilized to secure the lead assembly 181 to the stud 1030. Moreover, in some embodiments, the clip 1030 is not utilized, but instead, another stop 1022 is utilized in its place, and a second section of the lead assembly is utilized, analogous to that of FIG. 10. The stud is thus past through the hole in the lead assembly 181, and the stop is placed on the opposite side of the shaft 1020 from the tragus, thus trapping the lead assembly 181 between the stop and the tragus.

Any arrangement that can be utilized to secure the lead assembly 181 to the tragus or other part of the auricle so as to prevent or otherwise limit the likelihood of the electrode array assembly 190 from being dislodged from the cochlea as a result of a force applied to the lead assembly 181 beyond the location where the lead assembly is secured can be utilized.

Figure 11:
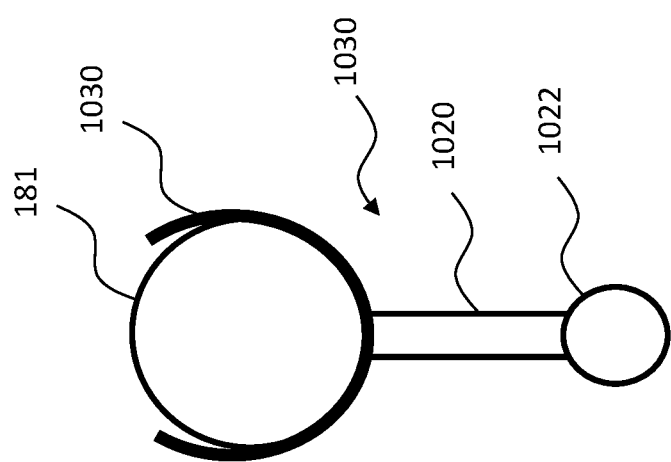

Note also that while the embodiments depicted above are directed towards securing the lead assembly 181 at a location of the outer ear, in an exemplary embodiment, the lead assembly 181 can be secured to tissue of the recipient in the middle ear location. In this regard, in an exemplary embodiment, a bone screw and fixture combination can be utilized to secure the lead assembly 181 in the middle ear. An exemplary embodiment of this is depicted in FIG. 11, where fixture 1130 includes a flanged assembly 1140 having a hole therethrough through which bone screw 1120 extends, such that the bone screw 1120 can be screwed into bone, trapping the flanged assembly 1140 between the bone and/or skin above the bone and the head 1122 of the bone screw. As can be seen, the assembly 1140 includes two walls extending 90° away from each other that seat the lead assembly 181. In the exemplary embodiment depicted in FIG. 12, adhesive 1150 is utilized to secure or otherwise attach the lead assembly 181 the assembly 1140. Other types of fixation between the lead assembly 181 and the assembly 1140 can be utilized in other exemplary embodiments, such as the clip of FIG. 11, etc.

Note also that the embodiment of FIG. 12 can also be utilized in the outer ear instead of the middle ear. A modicum of modification can have utilitarian value in at least some exemplary embodiments relative to the embodiment utilized in the middle ear. That said, in some alternate embodiments, the fixation device utilized for the middle ear can also be utilized in the outer ear without modification. Note also that in at least some exemplary embodiments, a fixation device is utilized in the middle ear and a separate fixation device is utilized in the outer ear. In this regard, the embodiments of FIGS. 10, 11 and/or 12 can be combined in use each securing a different section of the lead assembly 181 to the recipient.

Note also, in an exemplary embodiment, separate fixtures according to FIG. 12 can be utilized: one in the middle ear, and one in the outer ear.

In view of the above, in an exemplary embodiment, there is a hearing prosthesis as described above and/or below, further comprising a connector, such as that depicted in FIGS. 10, 11, and/or 12, configured to retain a portion of the lead assembly relative to the outer ear or the middle ear when the portion of the lead assembly is located in the outer ear or middle ear, respectively. Still further, in view of the above, in an exemplary embodiment, there is a hearing prosthesis as detailed above and/or below, further comprising a connector, such as that described in the embodiments of FIGS. 10 and 9, configured to connect a portion of the lead assembly relative to the outer ear when the portion of the lead assembly is located in the outer ear via percutaneous connection to the tragus.

Figure 13:
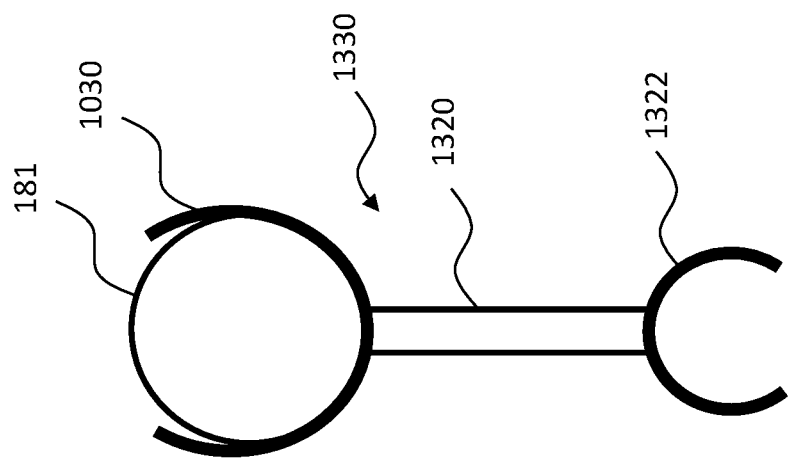

It is also noted that fixation regimes utilized in the middle ear to fix the electrode array to tissue of the recipient can utilize the ossicles. That is, in an exemplary embodiment, a connector can be connected to the ossicles so as to fix the electrode array assembly to the ossicles, thus preventing the electrode array assembly from moving as a result of a force applied to the lead assembly in the matters detailed above and variations thereof. FIG. 13 depicts an exemplary embodiment of a connector 1330 that can be connected to the ossicles. In an exemplary embodiment, clip 1322 is malleable, and can be bent around the ossicles so as to secure support stud 1320 thereto. At the opposite and of stud 1320 is clip 1030, which is used in the manner concomitant with that detailed above. In this regard, it is also noted that in some alternate embodiments, clip 1030 is also malleable component that can be bent or otherwise deformed about the lead assembly 181 so as to secure the clip 1030 to the lead assembly.

Note also that the embodiment of FIG. 13 can be attached to the other components in the middle ear other than the ossicles, such as bony structures therein that enable the clip 1322 to be attached thereto. As with the other connectors detailed herein and variations thereof, the connector FIG. 13 can be utilized in combination with other connectors, whether such connectors are utilized in the outer ear or the middle ear, etc.

Note also that embodiments can utilize connectors that connect to the outer wall of the cochlea/the interface between the inner here and the middle ear. Further, as noted above, the electrode array assembly includes ridges 197 that enhance the securement of the electrode array assembly 190 in the cochlea.

In the embodiment of FIG. 8 and the related embodiments thereof, the embodiments can have utilitarian value in that no parts of the implantable portion and/or the implantable component of the electric hearing prosthesis are hermetically sealed or otherwise utilize a hermetic enclosure. This is because, with respect to at least some of the embodiments detailed herein, such is not needed because all of the components that could be damaged or otherwise experience a deleterious effect if exposed to body fluids and/or the internal environment of the recipient are located external to the recipient. This is not to say that the components of the implantable portions and/or implantable components are not isolated from each other and/or isolated from the ambient environment inside the recipient. Standard isolation practices are implemented. It is that these isolation practices do not correspond to hermetic isolation. In this regard, it is to be understood that one lead is isolated from another lead, and that one electrode contact is isolated from another electrode contact. However, it is that these components are not hermetically sealed from the ambient environment. This is as opposed to the stimulator of the receiver—stimulator 180 of the embodiment of FIG. 1B, where the stimulator 180 will be encased in a housing that is hermetically sealed from the ambient environment so as to protect the electronic components therein (in some embodiments, the housing will include feedthroughs to place the lead wires of the lead assembly into electrical communication with the electronic components located inside the housing).

Accordingly, in an exemplary embodiment, there is a hearing prosthesis as detailed herein, wherein there is no hermetic enclosure in any part of the implantable portion and/or implantable component. Indeed, in an exemplary embodiment, there is a hearing prosthesis as detailed herein wherein there is no hermetic enclosure, even with respect to the external portions and/or the external components. In this regard, the hearing prosthesis can be devoid of hermetic enclosures, or at least the implantable portions and/or implantable components can be devoid of hermetic enclosures.

As noted above, all of the sound processing componentry and the stimulator componentry are located external to the recipient in at least some exemplary embodiments. Thus, in an exemplary embodiment, there is an electric hearing prosthesis, comprising an implantable portion configured to electrically stimulate a cochlea to evoke a hearing percept (e.g., the electrode array assembly 190 and the pertinent portions of the lead assembly 181). This electric hearing prosthesis further includes an external portion configured to be in wired communication with the implantable portion (e.g., the portions of the lead assembly 181 located outside the tympanic membrane, the connector 332 and the BTE 340 to which the connector is connected. In this exemplary embodiment, the electronic components of the implantable portion are all passive electronic components. This is as opposed to active electronic components.

A passive electronic component is a component that does not require energy to operate, except for the available alternating current (AC) circuit or direct current (DC) that it is connected to. A passive component is not capable of power gain and is not a source of energy. Generally, passive components are not able to increase the power of a signal nor are they able to amplify the signal. However, they can increase current or voltage via storage of electrical energy from resonant frequencies or by a transformer that acts like an electrical isolator. In an exemplary embodiment, the passive circuit, and/or a passive circuit portion (a portion of a circuit) is a lossless circuit and/or a lossless circuit portion, in that it does not have an input or output net power flow.

Passive components that use circuit architecture would include inductors, resistors, voltage and current sources, capacitors, and transformers. Likewise, passive filters are comprised of four elementary linear elements that include an inductor, capacitor, resistor, and transformer. Some high-tech passive filters can have non-linear elements like a transmission line.

Corollary to the above, in an exemplary embodiment, there is an electric hearing prosthesis, such as any of those detailed herein and/or variations thereof, that include an implantable component/implantable portion, that is devoid of any integrated circuits. Still further, in an exemplary embodiment, there is an implantable component/portion of an electric hearing prosthesis that does not include any electronic assemblies.

It is noted that while the passive electronic component teachings above have been directed towards the implantable component, these teachings are also applicable to at least portions of the external portions, such as the remainder of the lead assembly 181 and the connector 332.

Figure 14:
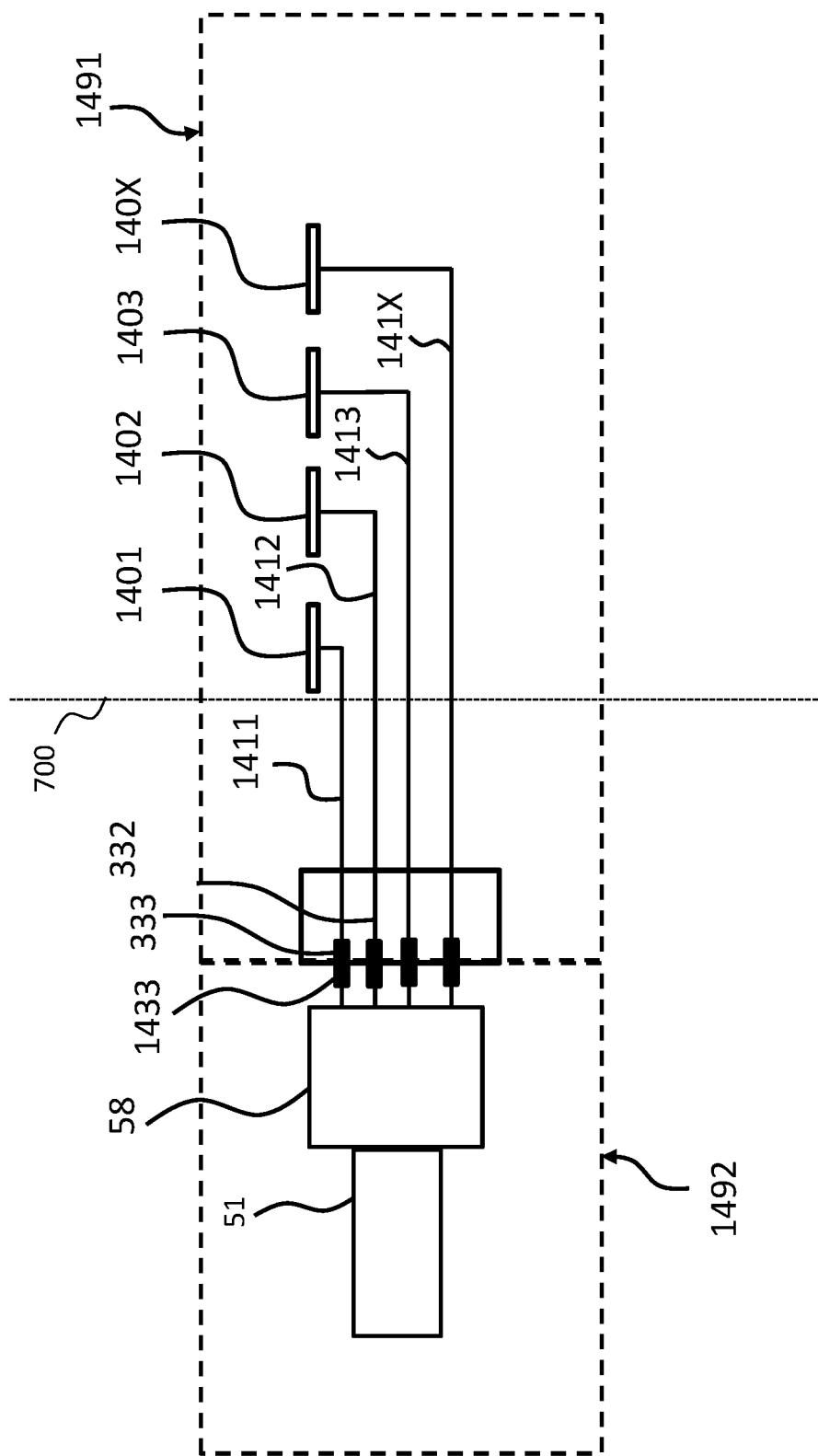
FIGS. 14 and 15 are schematics of circuit portions according to exemplary embodiments.

In this regard, FIG. 14 depicts by way of functional diagram a first circuit portion 1491 and a second circuit portion 1492 of an exemplary electric hearing prosthesis according to some of the embodiments detailed herein. Here, the boundaries of the first circuit portion 1491 (the dashed box labeled 1491) extend from the connector subcomponents 333 for each lead of the connector 332 that interface with respective connector subcomponents 1433 in the external device 340 (to place each lead into wired electrical communication with corresponding leads or circuit traces of the external device 340), to and inclusive of the electrode contacts 1401, 1402, 1403 and 140X (typically, 22 electrode contacts) of the electrode array assembly 190 (where the electrode contacts correspond to elements 148 of FIGS. 2B and 2, etc.). The first circuit portion also includes the leads 1411, 1412, 1413, and 141X that respectively extend from the respective connector subcomponents 333 to the respective electrode contacts.

Briefly, it is noted that in an exemplary embodiment, the connector subcomponents 333 connector prongs that extend into female prongs of connector subcomponents 1433 of the external device 340, and thus make electrical contact therewith. In some alternate embodiments, the connector subcomponents 333 are female portions, and the connector subcomponents 1433 are male portions. Note also, the combination of the two can be utilized, where some of the connector subcomponents 333 are male and some are female, and vice versa for connector subcomponents 1433.

Also as can be seen in FIG. 14, second circuit portion 1492 extends from and inclusive of the connector subcomponents 1433 to include all other components of the external device 340 (the sound processor 51, the stimulator 58 (if present and distinct from the sound processor 51, etc.).

Also superimposed on the schematic of FIG. 14 is the boundary line 700 representing the tympanic membrane. As can be seen, the first circuit portion 1491 extends from inside the recipient to a location outside the recipient.

In view of the above, it is to be understood that in an exemplary embodiment, the first circuit portion 1491 is a circuit portion that is devoid of active electronic components. Corollary to this is that the electronic components of the first circuit portion are all passive electronic components. Another way of stating this is that all portions of the electrical circuit (and/or all portions of the first electric circuit portion 1491) and/or all portions of the electrical circuits that is/are utilized to electrically stimulate the cochlea to evoke and electric hearing percept that are located inside the recipient/implanted/implantable in the recipient are made up of only passive electronic components and do not include any active electronic components. Another way of stating this is that no portion of any electrical circuit (and/or no portion of the first electric circuit portion 1491), which portion is implanted in the recipient, includes active electronic components. Yet another way of stating this is that any portion of any electrical circuit (and/or any portion of the first electric circuit portion 1491), which portion is implanted in the recipient, includes only passive electronic components.

Also, in an exemplary embodiment, it can be said that all portions of the electrical circuits located inside the recipient and/or all portions of the first electric circuit portion 1491 include only electrical leads and electrode contacts and, if present (e.g., some embodiments can be such that the electrical leads of the electrical contacts are monolithic components, and thus no bonding is present between the two components), the bonding components that place the electrical leads into wired communication with the electrical contacts, and, if applicable, the respective insulators thereof. This is as distinct from portions of the electrical circuits that are located outside the recipient (which can be part of the same circuit of which the implanted portion is a part). In an exemplary embodiment, it can be said that all portions of the electrical circuits located inside the recipient (and/or all portions of the first electric circuit portion 1491) comprise only conductive components and/or electrically conductive metals and/or metal alloys and, if applicable, the respective insulator components. In an exemplary embodiment, it can be said that all portions of the electrical circuits located inside the recipient (and/or all portions of the first electric circuit portion 1491) comprise only conductive components and, if present, insulator components.

In an exemplary embodiment, it can be said that all portions of the electrical circuits located inside the recipient (and/or all portions of the first electric circuit portion 1491) do not include resistors (fixed or variable), beyond that which exists naturally owing to the natural resistance in the electrical leads and/contacts, capacitors, magnetic inductive devices, memristors, transducers, antennas, oscillators, and/ or any electromechanical devices (all beyond that which might exist naturally owing to the natural features associated with the electrical leads and/or contacts and/or the natural features associated with the electrical insulation thereof.)

In an exemplary embodiment, it can be said that all portions of the implantable portions of the electric hearing prosthesis consist or consist essentially of the lead wires, the material utilized to insulate the lead wires from one another and from the ambient environment, and any unifying components that hold the lead wires, insulated or otherwise, together, if present, the associated electrode contacts, the support for the electrode contacts (e.g., silicone support forming the chassis supporting the electrodes of the electrode array assembly, and, if present, a stylus and, if present, a connector component or components (e.g., as detailed herein).

In an exemplary embodiment, it can be said that all portions of the implantable portions of the electric hearing prosthesis consist or consist essentially of conductive metals and/or metal alloys in the form of wires and conductive traces, and non-electronic components (e.g., silicone supporting the contacts, stylus, the lead chassis, etc.).

Figure 15:
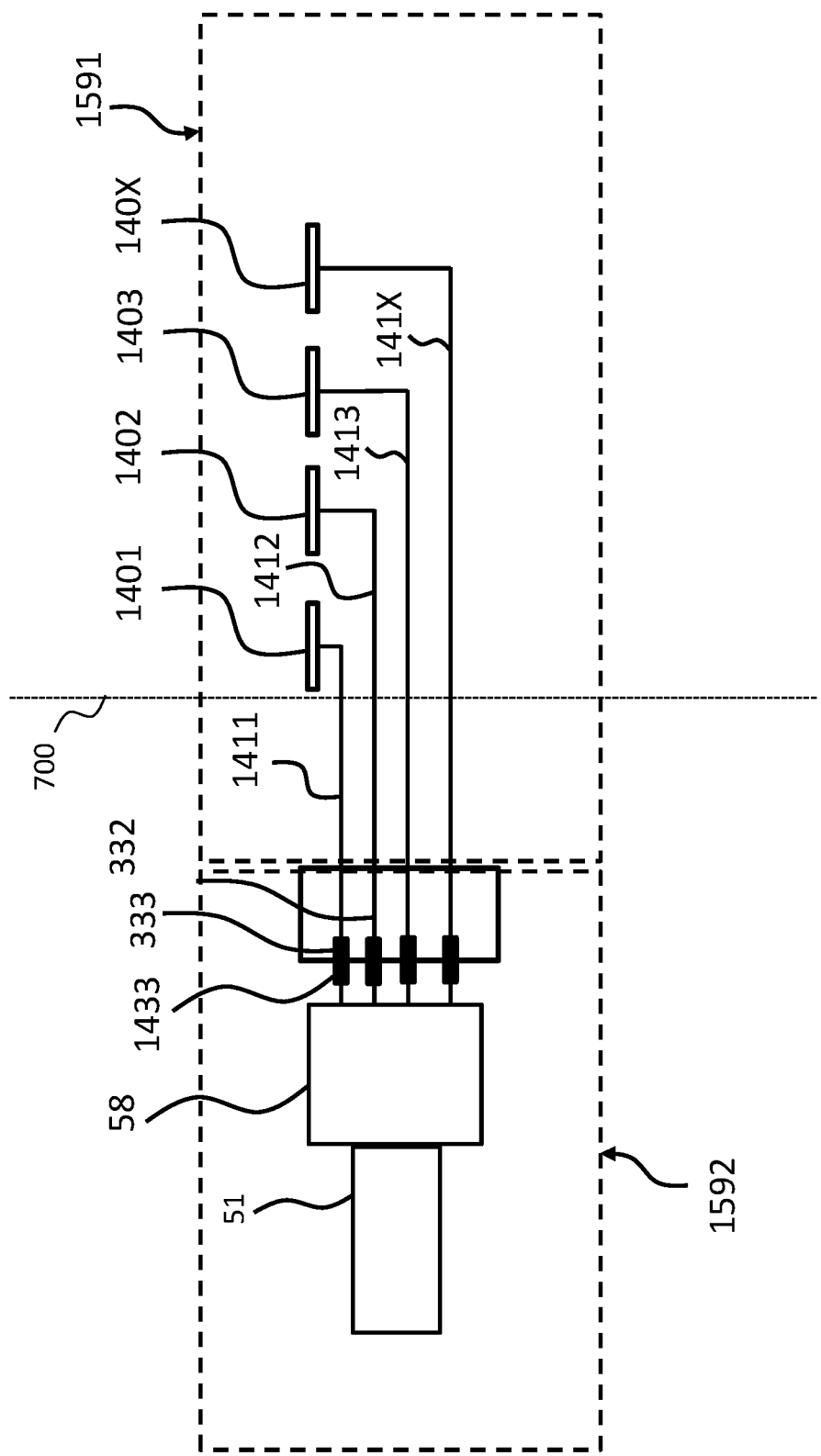

FIG. 15 depicts an alternate embodiment where a first electrical circuit portion 1591 extends not from the subcomponents 333 of the connector 332, but from the point at which the leads enter the connector 332. In an exemplary embodiment, this first electrical circuit portion 1591 can extend from the point where the leads first contact the subcomponents 333. As can be seen, the second electrical circuit portion 1592 extends to the point at which the leads enter the connector 332. In an exemplary embodiment, the second electrical circuit portion 1592 can extend from the point where the leads first contact the subcomponents 333. All of the teachings detailed herein with respect to the first electrical circuit portion 1491 and second electrical circuit portion 1492 are applicable, respectively, to the first electrical circuit portion 1591 and the second electrical circuit portion 1592.

In the above, it can be seen that in an exemplary embodiment, all active electronic components of the electric hearing prosthesis are part of the external portion/external component (e.g., BTE device 340). In an exemplary embodiment, all active electronic components are located within the second electric circuit portion 1492.

Also in view of the above, it can be seen that in an exemplary embodiment, the implantable portion of the electric hearing prosthesis includes a lead assembly (e.g., lead assembly 181) extending from an electrode array of the implantable portion including a plurality of electrodes (e.g., electrode assembly 190), wherein the lead assembly includes a plurality of electrically isolated electrical circuit portions (e.g., those portions respectively corresponding to lead wire 1411 and contact 1401, lead wire 1412 and contact 1402, lead wire 1413 and contact 1403, and lead wire 140X and contact 140X, etc.) extending from a connector (e.g., connector 333) in wired electrical communication with the lead assembly to the respective electrodes (contacts 1401, 1402, etc.) of the electrode array in a wired manner.

Still further, in an exemplary embodiment of the electric hearing prosthesis, the implantable portion includes a plurality of electrically isolated circuit portions of the prosthesis each including a respective electrode of an electrode array of the implantable portion. In an exemplary embodiment, this corresponds, respectively, to the lead 1411 and contact 1401, etc., of FIG. 14. In this exemplary embodiment, all of the respective electrically isolated circuit portions consist essentially of one or more electrical lead portions, an electrode, and electrical conductivity features between the respective lead portion(s) and the electrodes. As noted above, in an exemplary embodiment, the external portion includes a sound processor in one of a BTE or an ITE, and the sound processor is in wired communication with electrodes of an electrode array of the implantable portion, the electrode array being configured to be placed into a cochlea of the recipient such that a plurality of electrodes are located in the cochlea. This is as opposed to the embodiment of FIG. 1A, where the sound processor is not in wired communication with the electrodes located in the cochlea, but instead is in communication therewith via the transcutaneous RF link.

Also, in an exemplary embodiment, the electric hearing prosthesis is such that the implantable portion consists of a lead assembly and an electrode array and/or is such that the implantable component consists essentially of a lead assembly and an electrode array and an electrical connector. Also, in an exemplary embodiment, the electric hearing prosthesis is such that the implantable portion consists of a lead assembly and an electrode array and one or more connectors configured to connect the lead assembly to tissue of the recipient and/or is such that the implantable component consists of or consist essentially of a lead assembly and an electrode array and an electrical connector and one or more connectors configured to connect the lead assembly to tissue of the recipient. Moreover, in an exemplary embodiment, the electric hearing prosthesis is such that the implantable portion is a portion only made up of components selected from the group consisting of a lead assembly, an electrode array and one or more connectors configured to connect the lead assembly to tissue of the recipient. In an exemplary embodiment, the electric hearing prosthesis is such that the implantable component is a component made up of only components selected from the group consisting of a lead assembly an electrode array (which can include a straightening element, such as a stylus or a sheath), an electrical connector, one or more fixation devices (such as a connector) configured to connect the lead assembly to tissue of the recipient, and an active electronics package (located between connector 332 and the electrode array assembly, and electrodes 1401 etc., in particular, in the external portion (as opposed to the implantable portion) of the implantable component). With respect to the latter, as will be detailed below, a device, such as component 1632 as will be described in greater detail below, can be utilized such that signals from a limited number of contacts from the sound processor (e.g., 3 or 4 or so—an amount more than or equal to 3 or 4 or 5 or 6 or 7 or 8 times less than the number of electrodes of the electrode array assembly) can be analyzed by the the active electronics package to assign stimulation signals to the 22 electrodes (or however many there are) of the electrode array assembly.

In some exemplary embodiments, the implantable portion is part of an implantable component (e.g., component 601). The implantable component consists of an assembly of components selected from the group consisting of (i) a connector (e.g., element 332) configured to connect to an external component of an external portion of the prosthesis containing active electronic components (e.g., external device 340 of external component 602), (ii) electrodes (e.g., contacts 148), (iii) respective leads extending from the respective electrodes to the connector (e.g., lead wires 189), (iv) respective insulator components for the leads and/or electrodes and/or respective support components for the leads and/or electrodes (e.g., the insulators of the leads, the silicone of the electrode array assembly (sometimes referred to as an electrode carrier), etc., (v) one or more fixation devices configured to connect the implantable portion to tissue of the recipient (e.g., any of the connectors of FIGS. 9-13, (vi) body interface portions configured to interface the support components with tissue of the recipient (e.g., groves 197), (vii) a stylus (e.g., element 191, if present) and/or a sheath, (viii) the active electronics package noted above and further detailed below, and (ix) electrode positioning maintenance components (e.g., stiffening structures located in the electrode array assembly).

In view of the above, it is to be understood that in an exemplary embodiment, the hearing prosthesis includes an external sound processor in wired signal communication with the electrodes of the electrode array. Further, the external sound processor is part of an external portion of the hearing prosthesis, the electrode array is part of an implantable portion of the hearing prosthesis, and the implantable portion of the hearing prosthesis is devoid of active electronic components.

Figure 16:
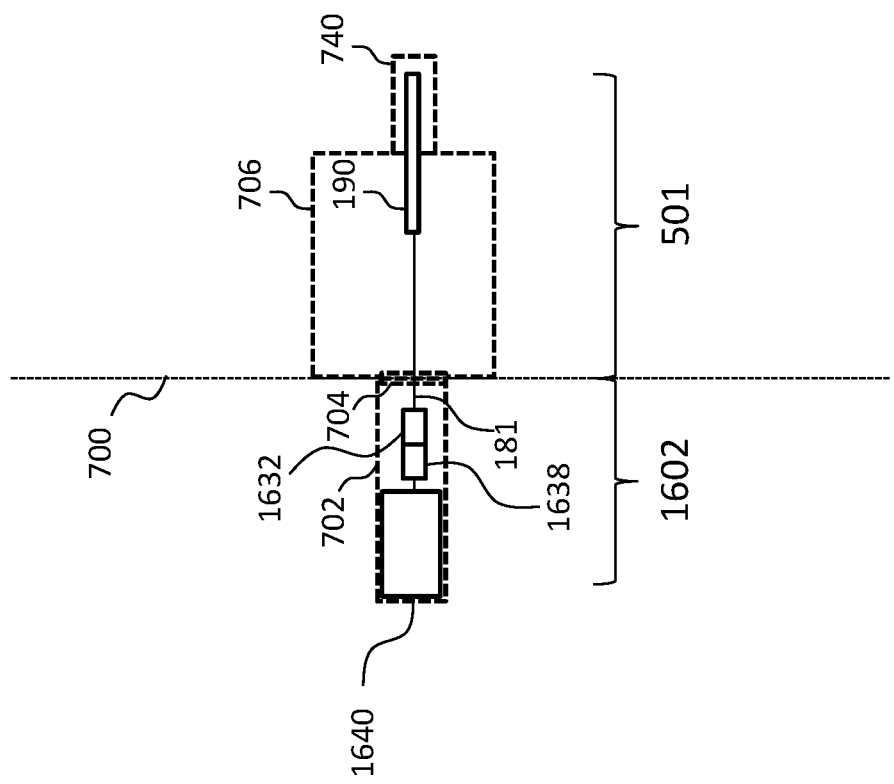
FIG. 16 is an exemplary functional schematic of an in the ear device electric hearing aid.

As noted above, some exemplary embodiments are utilized with external components that include in the ear (ITE) devices instead of and/or in addition to behind the ear (BTE) devices. In this regard, FIG. 16 functionally depicts an exemplary embodiment of a system of an electric hearing prosthesis that utilizes an ITE device, along with functional representations of the pertinent portions of the anatomy of the recipient. In this regard, the frame of reference of FIG. 16 corresponds to that of FIG. 8 detailed above with respect to the BTE device. Here, ITE device 1640 is connected via connector 1638 to connector 1632 which is connected to lead assembly 181. As can be seen, the connector 1632 is located inside the ear canal 702. Here, the implantable portion 501 corresponds to that detailed above, but the external portion corresponds to those elements making up portion 1602. That said, the implantable component will correspond to connector 1632, lead assembly 181, an electrode array assembly 190, whereas the external component will correspond to the ITE device 1640, the connector 1638, and the lead (not labeled) connecting the connector 1638 to the ITE device 1640. It is noted that in an alternate embodiment, the connector 1638 can be hard mounted to the ITE device 1640. That is, the connector 1638 can be an integral part of the ITE device 1640. Corollary to this is that in an exemplary embodiment, the connector of the BTE device detailed above can be a component that is located remote from the BTE device and connected thereto via a lead in a manner consistent with the teachings of FIG. 16, albeit as modified to accommodate the utilization of a BTE device instead of an ITE device. In an exemplary embodiment, the implantable portion 501 corresponds to the portion of the elongate simulative assembly of the Nucleus 5™ cochlear implant manufactured by Cochlear LTD of Australia and implanted into recipients in the United States pursuant to approval of the FDA in the years 2014, 2015, or 2016, located about 1.0, 1.5, 2.0, 2.5, 3.0, 3.5, or 4 inches away from the receiver/stimulator thereof to the distal end of the electrode array.

Figure 17:
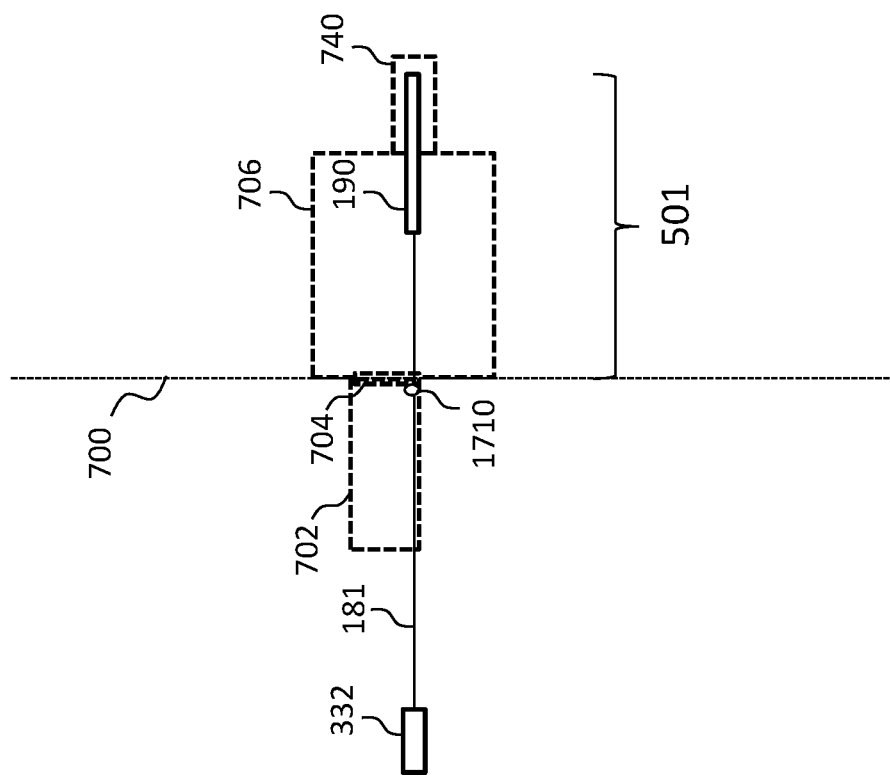
FIG. 17 is an exemplary functional schematic of an implantable component as positioned in the outer, middle and inner ear.

As briefly mentioned above, some exemplary embodiments utilize a stop device or the like that interfaces with the tympanic membrane so as to prevent movement of the lead assembly 181 relative to the tympanic membrane. In this regard, FIG. 17 depicts an exemplary embodiment by way functional representation, where a stop at 1710 is located about the electrode array 181, which stop abuts the outside of tympanic membrane 704 and prevents migration of the lead assembly 181 into the middle ear cavity 76. Alternatively, and/or in addition to this, a stop can be located about the electrode array 181, which stop abuts the inside of the tympanic membrane 704, and prevents migration of the lead assembly 181 out of the middle ear cavity 706. Of note is that of FIG. 17 depicts the lead assembly 181 extending to the tympanic membrane at an outer periphery thereof. There can be utilitarian value with respect to inserting the lead assembly through and/or otherwise puncture in the tympanic membrane at the periphery thereof as opposed to a more central location. In this regard, by way of example only and not by way of limitation, with respect to recipients that have residual hearing, locating the lead assembly 181 away from the central portion of tympanic membrane will permit the tympanic membrane to flex or otherwise vibrate in a more normal manner relative to that which would be the case if the lead assembly 181 extended through the center thereof or portions proximate the center thereof. In this regard, to the extent that the lead assembly 181 has a dampening effect on the tympanic membrane as a result of its extension therethrough, the dampening effect is lessened if the lead assembly 181 is located at the other periphery of the tympanic membrane.

Accordingly, in an exemplary embodiment, there is electric hearing prosthesis, wherein the hearing prosthesis includes a stop portion configured to interface with the tympanic membrane so as to secure a portion of the implantable portion relative to the tympanic membrane.

In an exemplary embodiment, the stop portion can be a spherical bead that extends about the lead assembly 181. This spherical bead can be integral with the lead assembly 181 (e.g., it can be an extension of the insulative material around the lead wires/a bulge in the insulative material, akin or otherwise analogous to element 181E of FIG. 10). This spherical bead can be separate from the lead assembly 181, and mechanically and/or chemically attached thereto. Alternatively, and/or in addition to this, the stop can be a flat circular plate or a square plate etc., through which the lead assembly 181 extends. This plate can also be integral with the lead assembly 181, concomitant with the bead detailed above. The plate can have features that change position when passing through a hole in the tympanic membrane. For example angled protrusions which push flat against the lead when passing through a hole and spring out to form a stop.

In an exemplary embodiment, a clip like device or the like can be placed on or about the lead assembly 181 after the lead assembly 181 is extended through the tympanic membrane/the hole in the tympanic membrane placed therein during the surgery procedure (more on this below). In these embodiments, the stop is fixed to the lead assembly such that the lead assembly will not move without the stop moving as well, barring some form of destructive deformation of the assembly. Thus, the stop will fix the lead assembly relative to the tympanic membrane providing that the stop cannot move relative to the tympanic membrane, at least in one direction.

Figure 18:
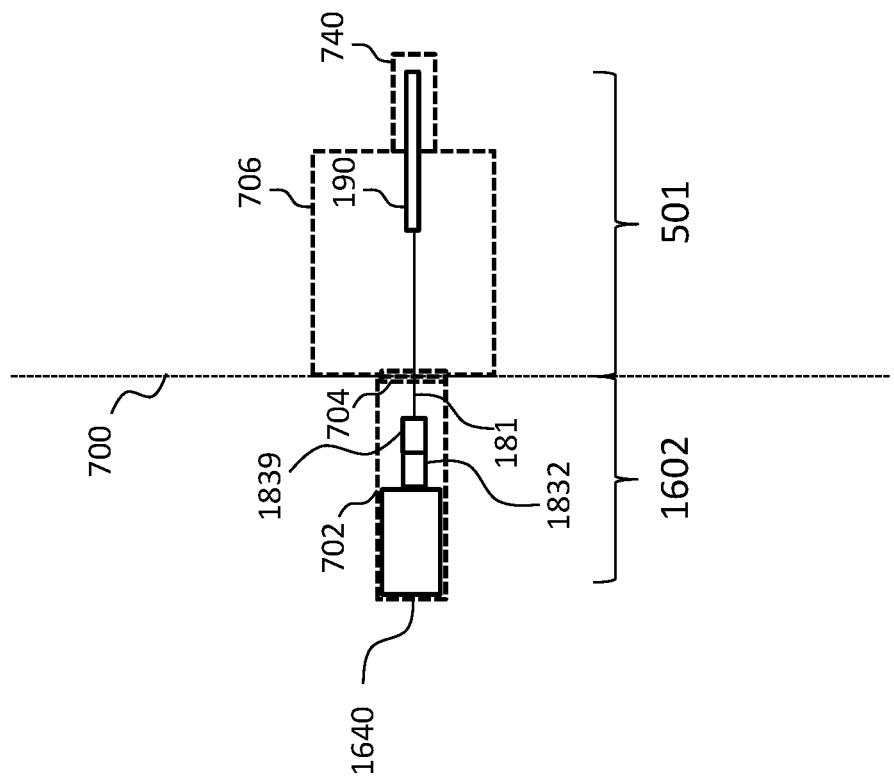
FIG. 18 is an exemplary functional schematic of an in the ear device electric hearing aid.

With reference back to FIGS. 16 and 17, it is noted that there can be utilitarian value with respect to utilizing a multiplexing regime or the like vis-à-vis placing the leads of the lead assembly 181 into wired communication with the external device in the form of an ITE device. In this regard, the connector 1632 and/or 1638 are configured to be located in the ear canal 702 of the recipient. This is a relatively tiny area in which the connector is to be located, which connector can have 22 or more separate sub-connection components (one for each of the 22 leads for the respective 22 electrodes, plus one or more leads for the return electrodes). This could result in 23 or 24 or more separate connections that should be electrically isolated from one another. Accordingly, there can be utilitarian value with respect to reducing the number of separate connections to be electrically isolated from one another, thus reducing the size of the connector 1632 and/or 1638. In this regard, FIG. 18 depicts an exemplary system that utilizes a connector 1832 that is part of the implantable component (where the connector of the ITE device 1640 is an integral part thereof), which also includes a multiplexer component 1839. In this exemplary embodiment, the connector 1832 includes no more than 2 or 3 or 4 or 5 or 6 or 7 or 8 or 9 or 10 or 11 or 12 or 13 separate sub-connector components, depending on the embodiment. Multiplexer 1839 receives signals from these sub-connector components, and analyzes these signals and break them up and otherwise divides the signals into respective signals for the respective leads of the lead assembly 181.

In an alternate embodiment, instead of the utilization of hardwired connectors, a very short range but high-efficiency RF link is utilized to communicate between IT device 1640 and the implantable component. By way of example only and not by way of limitation, element 1638 can instead be a high-efficiency RF transmitter and element 1632 can be a high-efficiency RF receiver. Moreover, in an exemplary embodiment, element 1632 can include a stimulator device. In this regard, by way of example only and not by way of limitation, element 1632 can function according to the receiver/stimulator 180 detailed above, an element 1638 can function according to the RF transmitter of the embodiment of FIG. 18 detailed above. Such can have utilitarian value with respect to reducing (in this embodiment, eliminating) the need for sub-connector components which could crowd or otherwise be difficult to implement in the limited space within the ear canal 702.

Figure 19:
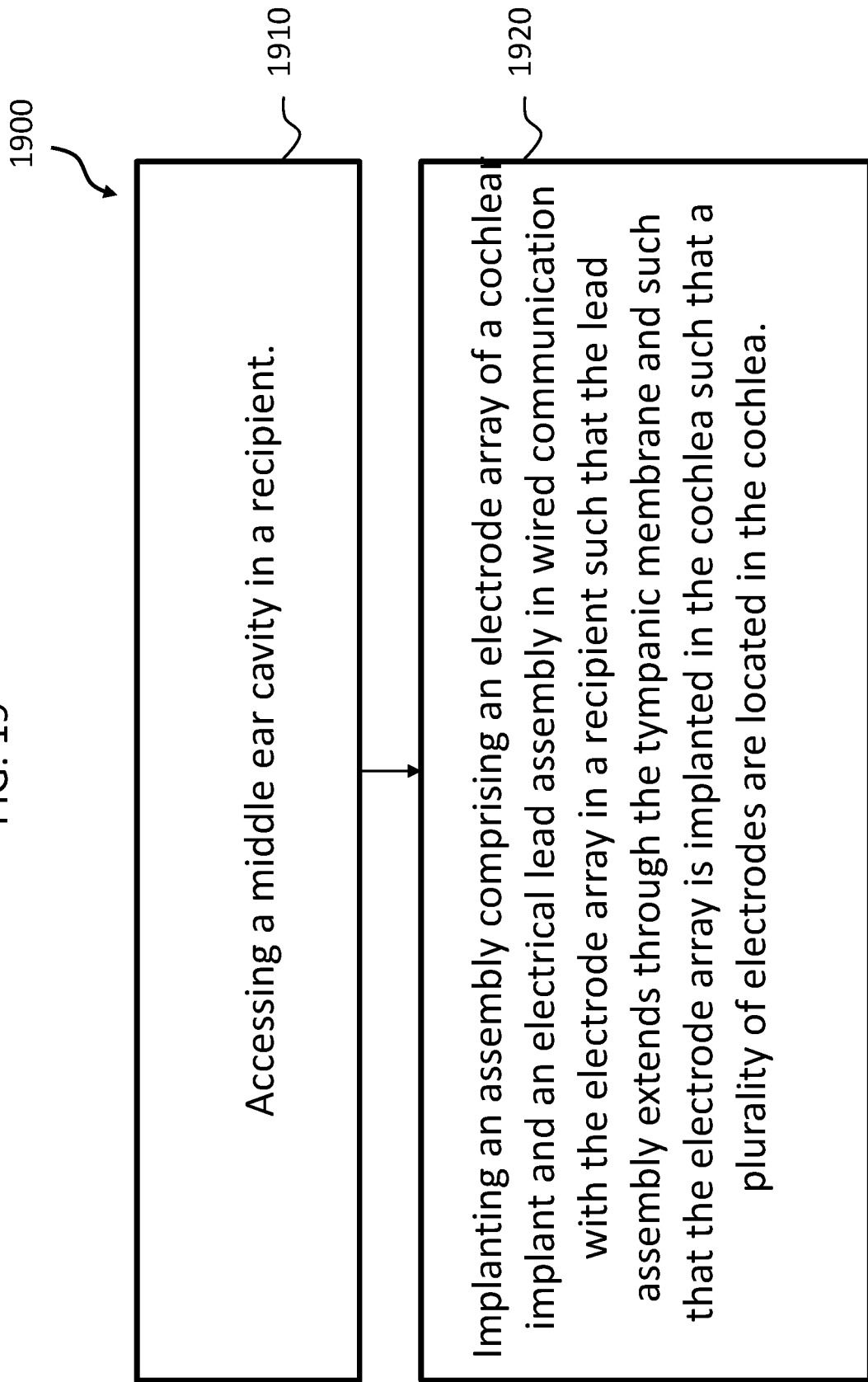
FIG. 19 is a flowchart for an exemplary method.

FIG. 19 presents an exemplary flowchart for an exemplary method, method 1900, according to an exemplary embodiment. Method 1900 includes method action 1910, which entails accessing a middle ear cavity in a recipient. As will be detailed below, in an exemplary embodiment, this entails creating an artificial opening in the tympanic membrane such that the middle ear cavity can be accessed from the ear canal of the recipient. Method 1900 further includes method action 1920, which entails implanting an assembly comprising an electrode array (e.g., electrode array assembly 190) of a cochlear implant and an electrical lead assembly (e.g., lead assembly 181) in wired communication with the electrode array in a recipient such that the lead assembly extends through the tympanic membrane and such that the electrode array, which includes a plurality of electrodes, is implanted in the cochlea such that a plurality of electrodes are located in the cochlea, wherein the plurality of electrodes are in wired communication with separate respective leads of the lead assembly. By way of example only and not by way of limitation, in an exemplary embodiment, the electrode array includes at least 7, 8, 9, 10, 11, 12, 13, 14, 15, 16, 17, 18, 19, 20, 21, or 22, or more electrodes. In an exemplary embodiment, all of the electrodes of the electrode array are located in the cochlea as a result of method action 1920. In an exemplary embodiment, only a subset of the electrode array located in the cochlea as a result of method action 1920, which subset includes a plurality of electrodes.

In an exemplary embodiment, method 1900 further comprises the action of completing the implantation of the assembly without drilling into bone of the recipient. By way of example only and not by way of limitation, method 1900 instead comprises the action of completing the implantation of the assembly without drilling into the mastoid bone and/or temporal bone of the recipient. That said, in an exemplary embodiment, method 1900 instead comprises the action of completing the implantation of the assembly without drilling into bone of the recipient other than holes for fixation screws used to attach portions of the lead assembly to tissue of the recipient and/or other than fixation passageways for clips or the like used to attach portions of the lead assembly to tissue of the recipient. By way of example only and not by way of limitation, such a fixation screw can correspond to the fixation screw 1120 of FIG. 12 above. Still further by way of example only and not by way of limitation, such clips can correspond to the clip of FIG. 13 above.

In an exemplary embodiment, method 1900 further includes the action of creating an artificial opening in the tympanic membrane. Indeed, in an exemplary embodiment, this action corresponds to the action of accessing a middle ear cavity in the recipient (method action 1910). In an exemplary embodiment, the opening in the tympanic membrane is concomitant with an opening created for drainage grommets in surgeries for people who require drainage or drying of fluid out of the middle ear or otherwise require pressure relief from the middle ear cavity through the tympanic membrane to the ambient environment. By way of example only and not by way of limitation, the opening created is about 1.5 mm in maximum diameter. In an exemplary embodiment, the opening created is about 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, or 2.2 mm in maximum diameter. In an exemplary embodiment, the entire electrode array assembly 190 is fed through this artificial opening from the outer ear into the middle ear cavity. Indeed, prior to this, a cochleostomy or an opening in the round window or the oval window of the cochlea is performed through this incision in the tympanic membrane, or more accurately, the tools that are utilized to create the opening in the cochlea are inserted through the incision in the tympanic membrane, and manipulated by mechanical extension through the insertion of the tympanic membrane so as to create the requisite opening in the cochlea so as to extend the electrode array therethrough. In this regard, method 1900 can be considered a minimally invasive surgical procedure, at least relative to a conventional cochlear implant implantation.

Accordingly, in an exemplary embodiment, method 1900 includes the action of inserting the electrode array through the incision in the tympanic membrane, followed by inserting the implantable portion of the lead assembly through the tympanic membrane. Corollary to this is that method 1900 includes the action of inserting the electrode array into the cochlea by manipulating the electrode array utilizing tools extending through the incision of the tympanic membrane. Thus, an exemplary embodiment of method 1900 further includes the action of making an artificial incision in the tympanic membrane, extending the electrode array through the artificial incision, after extending the electrode array through the artificial incision, inserting the electrode array into the cochlea such that the plurality of electrodes are inserted into the cochlea. In this exemplary embodiment, the electrode array is manipulated via forces directed through the artificial incision in the tympanic membrane.

That said, in some alternate embodiments, an incision through the skin of the recipient located away from the ear canal approximate thereto is created so as to access the middle ear. In this exemplary embodiment, instead of moving the electrode array and/or the lead assembly through an incision in the ear canal, the electrode array and/or the lead assembly is moved through this incision which bypasses the ear canal. In an exemplary embodiment, the middle ear of the recipient can be reached without drilling into bone. This includes accessing the middle ear by elevating the skin of the ear canal and passing the electrode array under the skin.

Because the embodiments detailed herein can be implemented via extension of the electrode array and the associated lead assembly into the middle ear and thus into the cochlea from the outer ear in general, and the ear canal in particular, or from around the outer ear but through the skin of the recipient into the middle ear cavity, some exemplary embodiments of method 1900 can be executed utilizing only local anesthetics. That is, by way of example only and not by way of limitation, method 1900 is such that the implantation is executed on a recipient under only local anesthetics, which recipient is not suffering from any other ailment beyond a hearing defect. That is, all things being equal, the recipient has a physiological state both chronically and acutely vis-à-vis the time of the surgery that, all things being equal, would not prevent the recipient from being sedated with anesthesia that effectively "knocks out" the patient, anesthesia beyond local anesthetics. This is as opposed to a physiological state that would prevent the recipient from being provided such anesthesia. In an exemplary embodiment, by way of example only and not by way of limitation, the recipient (patient) is a patient that would be mandated by the FDA in the United States to be placed under full anesthesia for a traditional cochlear implant surgery. In an exemplary embodiment, by way of example only and not by way of limitation, the recipient is a person less than 3 years of age, 3 years to 12 years of age, 12 years to 18 years of age, 18 years to 65 years of age, or 65 years and older in age, who is a $10^{th}$ percentile to $90^{th}$ percentile person health-wise for that age group save for the hearing deficiencies warranting the method 1900.

Consistent with the teachings detailed above vis-à-vis the connectors used to connect the lead assembly to the external component, in an exemplary embodiment, the lead assembly utilized in method 1900 includes at least 7 separate lead wires respectively connected to at least 7 separate electrodes of the electrode array, wherein all 7 separate electrodes are inserted into the cochlea. That said, in an exemplary embodiment, the lead assembly utilized in method 1900 includes at least 8 leads and electrodes, 9 leads and electrodes, 10 leads and electrodes, 11 leads and electrodes, 12 leads electrodes, 13, 14, 15, 16, 17, 18, 19, 20, 21, or 22, or more leads and electrodes, where the respective leads are respectively connected to the respective separate electrodes. Still further, a connector is connected to the lead assembly. In an exemplary embodiment, method 1900 further comprises, after the action of implanting the assembly, connecting an external device to the connector at a location outside the tympanic membrane relative to the middle ear and the inner ear of the recipient. By way of example only and not by way of limitation, this external device is an ITE or a BTE device as detailed above.

Still further, in an exemplary embodiment of method 1900, method 1900 further includes the action of fixing the electrical lead assembly to tissue of the recipient. In an exemplary embodiment, this is executed utilizing the devices, systems, and methods detailed above with respect to FIGS. 9 to 13. That said, in an alternate embodiment, suturing or the like is utilized. Indeed, in an exemplary embodiment, the lead assembly 181 can be sutured to the inner wall of the ear canal. In an exemplary embodiment, the lead assembly 181 can be sutured to tissue, and/or bone, within the middle ear cavity of the recipient. Moreover, the lead assembly 181 can be sutured to the tragus of the ear, instead of or in addition to utilizing the ring system of FIG. 10 or the like. Any device, system, or method of securing a portion of the lead assembly to tissue of the recipient so as to prevent migration or otherwise so as to prevent a force imparted on the lead assembly 181 from dislodging the implant electrode array can be utilized in at least some exemplary embodiments.

Concomitant with the teachings detailed above with respect to placing only passive components in the recipient, and maintaining all active components in external portions of the hearing prosthesis, in an exemplary embodiment, method 1900 further comprises completing implantation of all implantable portions of an electric hearing prosthesis such that no active electronic components are implanted inside the recipient. Corollary to this is that in an exemplary embodiment, method 1900 further comprises completing implantation of all implantable portions of the electric hearing prosthesis such that with respect to the electronic components of the hearing prosthesis, only passive electronic components are implanted inside the recipient.

Note also that instead of, or in addition to, the utilization of the fixation devices, systems, methods detailed herein that are utilized to fix the lead assembly to tissue of the recipient, and exemplary embodiment entails providing excess lead assembly in the outer ear and/or in the middle ear beyond that which is needed to extend the lead assembly from the electrode array, once fully implanted, to an external component to which the lead assembly is to be placed into wired communication. By way of example only and not by way of limitation, this can entail providing a loop or a wave slacking in the portion of the lead assembly located in the middle ear. Still further by way of example only and not by way of limitation, alternatively and/or in addition to this, this can entail providing a loop or a wave slacking in the portion of the lead assembly located in the ear canal.

In an exemplary embodiment, there is a hearing prosthesis as described above and/or below, wherein the hearing prosthesis includes an external sound processor in wired signal communication with the electrodes of the electrode array, the external sound processor is part of an external portion of the hearing prosthesis, the electrode array is part of an implantable portion of the hearing prosthesis, and the implantable portion of the hearing prosthesis is devoid of active electronic components.

In an exemplary embodiment, there is a hearing prosthesis as described above and/or below, wherein the hearing prosthesis includes a stop portion configured to interface with the tympanic membrane so as to secure a portion of the implantable portion relative to the tympanic membrane.

In an exemplary embodiment, there is a hearing prosthesis as described above and/or below, wherein the implantable portion is part of an implantable component, the implantable component consisting of an assembly of components selected from the group consisting of (i) a connector configured to connect to an external component of an external portion of the prosthesis containing active electronic components, (ii) electrodes, (iii) respective leads extending from the respective electrodes to the connector, (iv) respective insulator components for the leads and/or electrodes and/or respective support components for the leads and/or electrodes, (v) a fixation device configured to connect the implantable portion to tissue of the recipient, (vi) body interface portions configured to interface the support components with tissue of the recipient, (vii) a stylus, and (viii) electrode positioning maintenance components. In an exemplary embodiment, there is a hearing prosthesis as described above and/or below, wherein the external portion includes at least one of: an RF transmitter and an RF receiver; or a device configured to expand a first number of signal channels to a second number of signal channels greater than the first number of signal channels.

In an exemplary embodiment, there is a method as described above, further comprising providing excess lead assembly in a middle ear and in the outer ear of the recipient beyond that which is needed to extend the lead assembly from the electrode array to an external component to which the lead assembly is to be placed into wired communication.

It is noted that any disclosure of any method of making any component herein corresponds to a disclosure of the resulting component. It is further noted that any disclosure of any method action herein corresponds to a disclosure of an apparatus configured to execute such disclosure. Is also noted that any disclosure of any apparatus and/or system herein corresponds to a method of utilizing and/or making such. Any feature of any embodiment detailed herein can be combined with any other feature of any other embodiment detailed herein, unless otherwise specifically noted to the contrary.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. An electric hearing prosthesis, comprising:
   an implantable portion configured to electrically stimulate a cochlea to evoke a hearing percept; and
   an external portion configured to be in wired communication with the implantable portion, wherein
   electronic components of the implantable portion are all passive electronic components,
   the external portion includes one or more sound capture device(s), and
   the electrical hearing prosthesis includes a device downstream from the one or more sound capture device(s) configured to expand a first number of signal channels to a second number of signal channels greater than the first number of signal channels.

2. The electric hearing prosthesis of claim 1, wherein:
   the external portion includes a sound processor in an in the ear device;
   the sound processor is in wired communication with electrodes of an electrode array of the implantable portion, the electrode array being configured to be placed into a cochlea of the recipient such that a plurality of electrodes are located in the cochlea, the wired communication being via an assembly that extends from the in the ear device down an ear canal towards the middle ear and then to the electrode array; and
   the prosthesis is configured such that signals from a limited number of contacts from the sound processor is analyzed to assign stimulation signals to a number of electrodes greater than the limited number of contacts, the electrodes being configured to stimulate tissue of a person to evoke a hearing percept.

3. The electric hearing prosthesis of claim 1, wherein:
   the hearing prosthesis includes a stop portion configured to interface with the tympanic membrane so as to secure a portion of the implantable portion relative to the tympanic membrane.

4. The electric hearing prosthesis of claim 1, wherein:
   the electric hearing prosthesis includes an external sound processor in wired signal communication with electrodes of the implantable portion, which electrodes are configured to electrically stimulate the cochlea to evoke the hearing percept;
   the external sound processor is part of an external portion of the electric hearing prosthesis;
   the implantable portion is devoid of active electronic components.

5. The electric hearing prosthesis of claim 1, wherein the external portion includes an external sound processor, wherein the electric hearing prosthesis does not include an RF communication component placing the sound processor into signal communication with electrodes of the implantable portion, which electrodes are configured to electrically stimulate the cochlea to evoke the hearing percept.

6. The electric hearing prosthesis of claim 1, wherein:
   the external portion includes the device downstream from the one or more sound capture device(s) configured to expand a first number of signal channels to a second number of signal channels greater than the first number of signal channels.

7. The electric hearing prosthesis of claim 1, wherein:
   the implantable portion includes a tissue stimulating component configured to stimulate ear tissue to evoke a hearing percept;
   a percutaneous lead assembly extends from tissue stimulating component to the external portion;
   a connector connects a first length of the lead assembly extending from the tissue stimulating component to a second length of the lead assembly extending from an external functional component of the external portion, the connector being configured to releasable connect the first length to the second length; and
   the hearing prosthesis is configured such that the connector is located in an ear canal when the tissue stimulating component is implanted at a location in the recipient to stimulate the ear tissue and the electric hearing prosthesis is used to evoke a hearing percept.

8. The electric hearing prosthesis of claim 1, wherein:
   the external portion includes an in the ear canal device;
   all external portions are configured to be located in an ear canal of a recipient; and a connector connects a first length of a lead assembly extending from a tissue stimulating device of the hearing prosthesis to a second length of the lead assembly extending from the in the ear canal device, the connector being configured to releasable connect the first length to the second length.

9. The electric hearing prosthesis of claim 1, wherein:
the implantable portion includes a tissue stimulating component configured to stimulate tissue to evoke a hearing percept;
a percutaneous wire extends from tissue stimulating component to the external portion;
a connector distinct from the wire, the connector connecting a first length of the wire extending from the tissue stimulating component to a second length of the wire extending from an external functional component of the external portion, the connector being configured to releasable connect the first length to the second length; and
the hearing prosthesis is configured such that the connector is located in an ear canal when the tissue stimulating component is implanted at a location in the recipient to stimulate the ear tissue and the electric hearing prosthesis is used to evoke a hearing percept.

10. The electric hearing prosthesis of claim 1, wherein:
the implantable portion consists of wire(s) and an electrode array.

11. An electric hearing prosthesis, comprising:
an implantable portion configured to electrically stimulate a cochlea to evoke a hearing percept; and
an external portion configured to be in wired communication with the implantable portion, wherein electronic components of the implantable portion are all passive electronic components, and wherein
the implantable portion includes a tissue stimulating component configured to stimulate ear tissue to evoke a hearing percept;
an RF transmitter is in wired signal communication with a functional component of the external portion;
an RF receiver is in wired signal communication with the tissue stimulator component; and
the hearing prosthesis is configured such that the RF transmitter and the RF receiver are fitted into an ear system of a recipient when the recipient is using the prosthesis to evoke a hearing percept.

12. The electric hearing prosthesis of claim 11, wherein:
the implantable includes an electrode array of a cochlear implant,
the prosthesis includes a lead assembly that is a percutaneous lead assembly and extends from the electrode array, and
a connector is located at an end of the lead assembly opposite the electrode array such that the connector is supported by only the lead relative to the recipient of the cochlear implant.

13. The electric hearing prosthesis of claim 11, wherein:
the implantable includes an electrode array of a cochlear implant,
the prosthesis includes a lead assembly that is a percutaneous lead assembly and extends from the electrode array, and
a connector is located at an end of the lead assembly opposite the electrode array such that the entire connector is completely outside a recipient of the cochlear implant when the electrode array is implanted in the cochlea.

14. The electric hearing prosthesis of claim 11, wherein:
the prosthesis includes a multiplexer component configured to be located in the ear system.

15. The electric hearing prosthesis of claim 14, wherein:
the multiplexer receives signals from a first number of leads, and analyzes these signals and breaks the signals up and/or divides the signals up into respective signals for respective second number of leads which lead to the tissue stimulating component, the second number of leads being at least twice the first number of leads.

16. The electric hearing prosthesis of claim 11, wherein:
the hearing prosthesis is configured such that the RF transmitter and the RF receiver are fitted into an ear canal of a recipient when the recipient is using the prosthesis to evoke a hearing percept, the RF transmitter providing a wireless signal to the RF receiver to evoke a hearing percept.

17. The electric hearing prosthesis of claim 11, wherein:
a percutaneous lead assembly extends from tissue stimulating component to the external portion;
a connector connects a first length of the lead assembly to a second length of the lead assembly; and
the connector includes a multiplexer component.

18. An electric hearing prosthesis, comprising:
an implantable portion configured to electrically stimulate a cochlea to evoke a hearing percept; and
an external portion configured to be in wired communication with the implantable portion, wherein
the hearing prosthesis is configured such that the only portion that extends from supercutaneous locations to subcutaneous locations extends through a tympanic membrane of a recipient of the prosthesis when the hearing prosthesis is implanted in a recipient, and
the electric hearing prosthesis further comprises:
a sound processor that is part of the external portion; and
a device configured such that signals from a limited number of contacts from the sound processor is analyzed to assign stimulation signals to a number of electrodes greater than the limited number of contacts, the electrodes being configured to stimulate tissue of a person to evoke a hearing percept.

19. The electric hearing prosthesis of claim 18, wherein:
the implantable portion includes a plurality of electrically isolated circuit portions of the prosthesis each including a respective electrode of an electrode array of the implantable portion; and
all of the respective electrically isolated circuit portions of the implantable portion consist essentially of one or more electrical lead portions, an electrode, and electrical conductivity features between the respective lead portion(s) and the electrodes.

20. The electric hearing prosthesis of claim 18, wherein:
the implantable portion consists of a lead assembly and an electrode array.

21. The electric hearing prosthesis of claim 18, wherein:
the implantable portion is an electrode array of a cochlear implant,
a lead assembly is a percutaneous lead assembly and extends from the electrode array to the external portion, and
the lead assembly is configured such that a portion of the lead assembly extends completely out of an ear canal of the via a supercutaneous route to a location behind a pinna of the recipient.

22. The electric hearing prosthesis of claim 18, wherein:
the external portion includes an in the ear canal device;
all external portions are configured to be located in an ear canal of a recipient;
a connector connects a first length of a wire, extending from a tissue stimulating device of the hearing prosthesis to the connector, to a second length of a wire extending from the in the ear canal device to the connector, the connector being configured to releasable connect the first length to the second length.

* * * * *